(12) United States Patent  
D'Agostino et al.

(10) Patent No.: US 9,320,601 B2  
(45) Date of Patent: Apr. 26, 2016

(54) METHOD AND APPARATUS FOR TREATING BONE FRACTURES, AND/OR FOR FORTIFYING AND/OR AUGMENTING BONE, INCLUDING THE PROVISION AND USE OF COMPOSITE IMPLANTS

(71) Applicants: Jeffrey A. D'Agostino, Deerfield, NH (US); Andrew J. Carter, Stow, MA (US); Arthur Watterson, Nashua, NH (US); Joseph P. Lane, Methuen, MA (US)

(72) Inventors: Jeffrey A. D'Agostino, Deerfield, NH (US); Andrew J. Carter, Stow, MA (US); Arthur Watterson, Nashua, NH (US); Joseph P. Lane, Methuen, MA (US)

(73) Assignee: 206 ORTHO, Inc., Lowell, MA (US)

( * ) Notice: Subject to any disclaimer, the term of this patent is extended or adjusted under 35 U.S.C. 154(b) by 0 days.

(21) Appl. No.: 13/781,473

(22) Filed: Feb. 28, 2013

(65) Prior Publication Data

US 2013/0253661 A1 Sep. 26, 2013

Related U.S. Application Data

(63) Continuation-in-part of application No. 13/452,273, filed on Apr. 20, 2012, now abandoned, which is a continuation-in-part of application No. PCT/US2011/057124, filed on Oct. 20, 2011.

(51) Int. Cl.  
*A61F 2/28* (2006.01)  
*A61K 9/00* (2006.01)  
*A61K 47/34* (2006.01)

(Continued)

(52) U.S. Cl.  
CPC ............... *A61F 2/28* (2013.01); *A61B 17/7097* (2013.01); *A61B 17/72* (2013.01); *A61K 9/0024* (2013.01); *A61K 47/34* (2013.01); *A61B 17/7275* (2013.01); *Y10T 428/13* (2015.01); *Y10T 428/249924* (2015.04); *Y10T 428/2915* (2015.01);

(Continued)

(58) Field of Classification Search  
CPC . A61K 9/0024; A61K 47/34; A61K 17/7097; A61K 17/72; A61K 17/7275  
USPC ........... 623/23.51; 428/292.1, 34.1, 365, 377, 428/396; 442/63; 523/115  
See application file for complete search history.

(56) References Cited

U.S. PATENT DOCUMENTS 534,293 A 2/1895 Stevens  
2,961,374 A 11/1960 Lieb et al.

(Continued)

FOREIGN PATENT DOCUMENTS

EP 0927214 7/2007  
EP 2 223 707 9/2010

(Continued)

OTHER PUBLICATIONS

M. Barry, J. M. H. Paterson "Flexible intramedullary nails for fractures in children" in the Journal of Bone & Joint Surgery, 2004, pp. 947-950.*

(Continued)

*Primary Examiner* — Blessing M Fubara  
(74) *Attorney, Agent, or Firm* — Pandiscio & Pandiscio

(57) ABSTRACT

A composite implant comprising an injectable matrix material which is flowable and settable, and at least one reinforcing element for integration with the injectable matrix material, the at least one reinforcing element adding sufficient strength to the injectable matrix material such that when the composite implant is disposed in a cavity in a bone, the composite implant supports the bone.

28 Claims, 23 Drawing Sheets

(51) Int. Cl.
*A61B 17/70* (2006.01)
*A61B 17/72* (2006.01)

(52) U.S. Cl.
CPC ...... *Y10T428/2936* (2015.01); *Y10T 428/2971* (2015.01); *Y10T 442/2033* (2015.04)

(56) References Cited

U.S. PATENT DOCUMENTS

| | | | |
|---|---|---|---|
| 4,241,537 A | | 12/1980 | Wood |
| 4,653,487 A | * | 3/1987 | Maale .................. 606/62 |
| 4,843,112 A | | 6/1989 | Gerhart et al. |
| 4,919,679 A | | 4/1990 | Averill et al. |
| 4,993,410 A | | 2/1991 | Kimsey |
| 5,064,427 A | | 11/1991 | Burkinshaw |
| 5,190,549 A | | 3/1993 | Miller et al. |
| 5,190,550 A | | 3/1993 | Miller et al. |
| 5,352,230 A | | 10/1994 | Hood |
| 5,409,492 A | | 4/1995 | Jones et al. |
| 5,443,471 A | | 8/1995 | Swajger |
| 5,458,641 A | | 10/1995 | Ramirez Jimenez |
| 5,476,466 A | | 12/1995 | Barrette et al. |
| 5,514,136 A | | 5/1996 | Richelsoph |
| 5,514,137 A | * | 5/1996 | Coutts .................. 606/62 |
| 5,549,679 A | | 8/1996 | Kuslich |
| 5,683,395 A | | 11/1997 | Mikhail |
| 5,725,580 A | | 3/1998 | Cloutier et al. |
| 5,739,176 A | | 4/1998 | Dunn et al. |
| 5,785,642 A | | 7/1998 | Wallace et al. |
| 5,849,015 A | | 12/1998 | Haywood et al. |
| 5,863,551 A | | 1/1999 | Woerly |
| 5,899,907 A | | 5/1999 | Johnson |
| 5,916,585 A | | 6/1999 | Cook et al. |
| 5,951,564 A | | 9/1999 | Schroder et al. |
| 5,989,259 A | | 11/1999 | Penenberg et al. |
| 6,110,179 A | | 8/2000 | Flivik et al. |
| 6,113,605 A | | 9/2000 | Storer |
| 6,165,177 A | | 12/2000 | Wilson et al. |
| 6,168,777 B1 | | 1/2001 | Greff et al. |
| 6,228,092 B1 | | 5/2001 | Mikhail |
| 6,238,435 B1 | | 5/2001 | Meulink et al. |
| 6,270,502 B1 | | 8/2001 | Stulberg |
| 6,521,736 B2 | | 2/2003 | Watterson et al. |
| 6,524,327 B1 | | 2/2003 | Spacek |
| 6,530,958 B1 | | 3/2003 | Cima et al. |
| 6,626,913 B1 | | 9/2003 | McKinnon et al. |
| 6,884,264 B2 | | 4/2005 | Spiegelberg et al. |
| 6,962,963 B2 | | 11/2005 | Kumar et al. |
| 7,037,311 B2 | | 5/2006 | Parkinson et al. |
| 7,494,491 B2 | | 2/2009 | Fankhauser et al. |
| 7,517,539 B1 | | 4/2009 | Lee et al. |
| 8,128,626 B2 | | 3/2012 | Justin |
| 8,348,956 B2 | | 1/2013 | Rabiner |
| 8,366,711 B2 | | 2/2013 | Rabiner et al. |
| 8,512,338 B2 | | 8/2013 | Rabiner et al. |
| 8,722,783 B2 | | 5/2014 | Rose et al. |
| 8,870,965 B2 | | 10/2014 | Rabiner et al. |
| 2003/0044467 A1 | | 3/2003 | Brodbeck et al. |
| 2003/0114552 A1 | | 6/2003 | Schacht |
| 2004/0010261 A1 | | 1/2004 | Hoag et al. |
| 2004/0010262 A1 | | 1/2004 | Parkinson et al. |
| 2004/0082954 A1 | | 4/2004 | Teitelbaum et al. |
| 2005/0081750 A1 | | 4/2005 | Xu et al. |
| 2005/0233062 A1 | | 10/2005 | Hossainy et al. |
| 2007/0059281 A1 | | 3/2007 | Moseley et al. |
| 2007/0191963 A1 | | 8/2007 | Winterbottom et al. |
| 2008/0004628 A1 | | 1/2008 | White |
| 2008/0051797 A1 | | 2/2008 | Surma et al. |
| 2008/0172061 A1 | | 7/2008 | Ragbir |
| 2008/0206716 A1 | | 8/2008 | Asgary |
| 2008/0221576 A1 | | 9/2008 | Keller |
| 2008/0228284 A1 | | 9/2008 | Fritz et al. |
| 2009/0099267 A1 | | 4/2009 | Kumar et al. |
| 2009/0182425 A1 | | 7/2009 | Duda et al. |
| 2010/0076503 A1 | | 3/2010 | Beyar et al. |
| 2010/0137491 A1 | | 6/2010 | Rose et al. |
| 2010/0331850 A1 | | 12/2010 | Rabiner |
| 2011/0013958 A1 | | 1/2011 | Shono et al. |
| 2012/0029102 A1 | | 2/2012 | Rose et al. |
| 2012/0095463 A1 | | 4/2012 | Rains et al. |
| 2012/0101593 A1 | | 4/2012 | D'Agostino et al. |
| 2012/0203264 A1 | | 8/2012 | Karwa et al. |
| 2012/0263797 A1 | | 10/2012 | D'Agostino et al. |
| 2013/0253661 A1 | | 9/2013 | D'Agostino et al. |

FOREIGN PATENT DOCUMENTS

| | | |
|---|---|---|
| WO | WO 92/20738 | 11/1992 |
| WO | WO 2010/011943 | 1/2010 |
| WO | WO 2014/190289 | 11/2014 |

OTHER PUBLICATIONS

A. Chen et al., Comparison of Biodegradable and Metallic Tension-Band Fixation for Patella Fractures: 38 Patients Followed for 2 Years, Acta Orthopaedica Scandinavica, 1998, pp. 39-42, vol. 69. No. 1.

J. C. Middleton et al., Synthetic Biodegradable Polymers as Orthopedic Devices, Biomaterials, 2000, pp. 2335-2346, vol. 21.

* cited by examiner

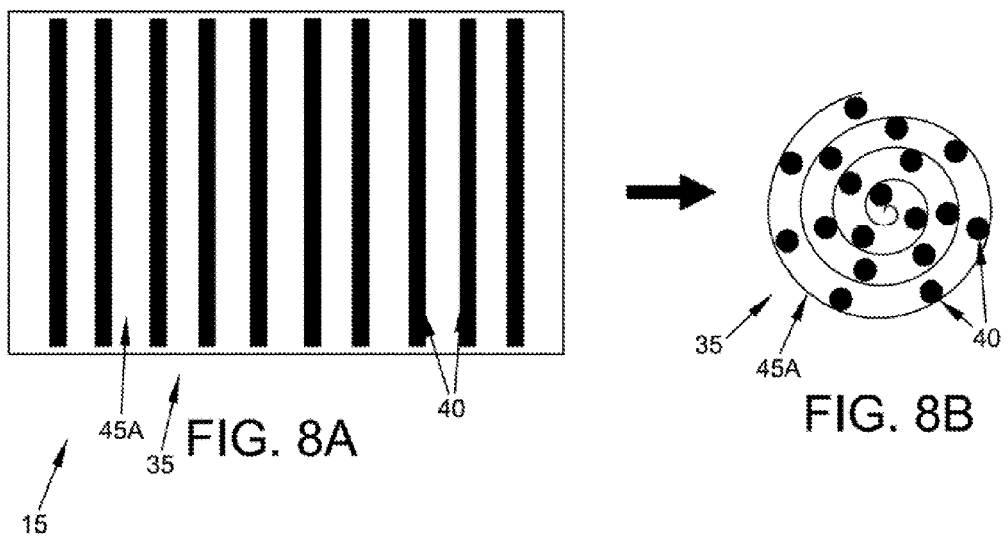

METHOD AND APPARATUS FOR TREATING BONE FRACTURES, AND/OR FOR FORTIFYING AND/OR AUGMENTING BONE, INCLUDING THE PROVISION AND USE OF COMPOSITE IMPLANTS

REFERENCE TO PENDING PRIOR PATENT APPLICATIONS

This patent application:

(i) is a continuation-in-part of pending prior U.S. patent application Ser. No. 13/452,273, filed Apr. 20, 2012 by Jeffrey A. D'Agostino et al. for IMPLANTABLE POLYMER FOR BONE AND VASCULAR LESIONS, which patent application in turn is a continuation-in-part of prior International (PCT) Patent Application No. PCT/US2011/057124, filed Oct. 20, 2011, which patent application in turn claims benefit of prior U.S. Provisional Patent Application Ser. No. 61/394,968, filed Oct. 20, 2010; and (ii) claims benefit of prior U.S. Provisional Patent Application Ser. No. 61/604,632, filed Feb. 29, 2012 by Jeffrey D'Agostino et al. for SPLINT INJECTION.

The four (4) above-identified patent applications are hereby incorporated herein by reference.

FIELD OF THE INVENTION

This invention relates to methods and apparatus for treating bones, and more particularly to methods and apparatus for treating bone fractures and/or for fortifying and/or augmenting bone in mammals.

BACKGROUND OF THE INVENTION

It is common for bones to become fractured as the result of a fall, an automobile accident, a sporting injury, etc. In these circumstances, it is common to reinforce the bone in the area of the fracture so as to support the bone during healing.

To this end, current treatment options typically comprise external stabilizers (e.g., plaster casts, braces, etc.) and internal stabilizers (e.g., screws, bone plates, intramedullary nails, etc.).

External stabilizers such as casts and external braces suffer from a number of disadvantages. For one thing, they can interfere with a patient's normal daily activities, e.g., it can be difficult to wear clothing over a cast, or to operate a motor vehicle with a cast, etc. Furthermore, with animals, external casting and bracing of some fractures can be extremely difficult. In addition, with external stabilizers, the soft tissue interposed between the bone and the external stabilizer is used to transmit load from the bone to the external stabilizer. As a result, shortly after application of the external stabilizer, the patient's intervening soft tissue will begin to atrophy through disuse, thereby requiring further rehabilitation for the patient. Furthermore, as the intervening soft tissue atrophies, the close supporting fit of the external stabilizer is disrupted and, as a result, effective load transfer is undermined.

Internal stabilizers such as screws, bone plates, intramedullary nails, etc. generally provide a more effective stabilization of the fracture, since they are able to directly interface with the bone. However, installing these internal stabilizers requires an invasive surgical procedure, e.g., a relatively large incision, etc. Furthermore, after healing of the fracture, the internal stabilizers (screws, bone plates, intramedullary nails, etc.) should, ideally, be removed so as to allow the bone to fully recover its mechanical strength. This, however, requires a second surgical procedure, with additional trauma to the patient.

In some circumstances (e.g., such as with fractures in vertebral bodies), bone cements may be injected into the interior of the bone in an attempt to stabilize the bone. However, such bone cements suffer from disadvantages of their own. More particularly, such bone cements are typically ceramic cements, polymer-based cements (e.g., polymethyl methacrylate, also known as PMMA) or calcium salt-based cements. While these bone cements are typically capable of withstanding significant compressive loading, they are also extremely brittle and typically cannot withstand significant tensile loading. This limits their application in instances where the loading on the bone may include a tensile component. This means that bone cements are not suitable for use in many situations, particularly in long bones (e.g., the tibia).

Thus it will be seen that a new approach is needed for treating bone fractures.

In addition to the foregoing, in some circumstances a medical condition (e.g., osteoporosis) can weaken or damage a bone, including the creation of voids within the bone, and it may be desirable to fortify and/or augment a bone so that it can better withstand the forces associated with normal physical activity. Unfortunately, however, the aforementioned external stabilizers, internal stabilizers and bone cements have all proven inadequate for fortifying and/or augmenting a bone, e.g., for the reasons given above.

Thus it will be seen that a new approach is also needed for fortifying and/or augmenting a bone.

SUMMARY OF THE INVENTION

The present invention provides a new approach for treating bone fractures.

The present invention also provides a new approach for fortifying and/or augmenting a bone.

More particularly, the present invention comprises the provision and use of a novel composite implant for treating bone fractures and/or for fortifying and/or augmenting a bone. The composite implant is disposed within the intramedullary canal of a bone, or within another opening in the bone, so as to function as an internal "splint", whereby to carry the stress created during patient activity. This allows a bone fracture to heal, or provides fortification and/or augmentation of a bone, with minimum inconvenience to the patient. The composite implant comprises a plurality of components that are introduced sequentially into the patient, and assembled in-situ, wherein each of the components has a size and flexibility which allows it to be installed using a minimally invasive approach while collectively providing the required structural reinforcement for the bone which is being treated. Significantly, the properties of the composite implant can be custom tailored for different treatment situations, e.g., the composite implant can have different lengths and/or different cross-sectional dimensions, the composite implant can have different compressive and/or tensile strengths, etc., all according to the individual needs of a particular patient.

In one preferred form of the invention, the composite implant comprises three components: a containment bag, one or more reinforcing elements and an injectable matrix material.

The containment bag serves to protect the remaining components of the composite implant from the ingress of blood and/or other bodily fluids that might interfere with the deployment of the one or more reinforcing elements and/or interfere with the deployment or solidification of the injectable matrix material. The containment bag also serves to constrain the flow of the injectable matrix material while the injectable matrix material is in its injectable state. The containment bag is flexible and may be fabricated from a resorbable polymer such as a polyurethane, polylactic acid, glycolic acid or some mixture/copolymer thereof. Alternatively, the containment bag may be formed from fibers that are woven, braided, knit, nonwoven, and/or otherwise worked so as to form a mesh bag. Suitable fibers include polylactic acid, polyglycolic acid, polydioxanone or mixtures/copolymers thereof. In any case, the containment bag preferably has sufficient strength to allow the injectable matrix material to be injected into the containment bag under substantial pressure so as to ensure good interfacial contact between the injectable matrix material and the one or more reinforcing elements, and to minimize voids within the containment bag, and to ensure good interfacial contact between the composite implant and the bone. Ideally the mesh bag is hydrophobic so as to minimize the ingress of bodily fluids into the containment bag that may otherwise interfere with the deployment or solidification of the various components of the composite implant. Alternatively, the mesh bag may have a limited porosity to allow some egress of the injectable matrix material out of the containment bag, e.g., to osseointegrate with the surrounding bone. The containment bag may have a hydrophobicity and porosity that affects the biocompatibility and degradation of the composite implant by modulating the ingress of water into the interior of the containment bag.

The one or more reinforcing elements comprise (i) flexible reinforcing sheets (which are preferably in the form of flexible concentric reinforcing tubes or flexible rolled reinforcing sheets), with the flexible reinforcing sheets comprising filaments formed into a textile (i.e., woven, braided, knit, nonwoven, and/or otherwise worked so as to form the flexible reinforcing sheets) or incorporated into a film so as to form the flexible reinforcing sheets, (ii) flexible reinforcing rods, with the flexible reinforcing rods comprising a plurality of filaments which are held together by an outer sheath of a textile or film (which may or may not have the same composition as the aforementioned flexible reinforcing sheets), or by a compacted (wound or compressed, etc.) connecting structure of a textile or film, or by a binder such as an adhesive, with or without surface projections for improved integration with the injectable matrix material, (iii) particulates (e.g., particles, granules, segments, nanotubes, whiskers, nanorods, etc.), or (iv) combinations of the foregoing. Where the one or more reinforcing elements comprise flexible reinforcing sheets and/or flexible reinforcing rods, the one or more reinforcing elements preferably have sufficient column strength to allow longitudinal delivery into the containment bag by pushing, and preferably have a configuration (e.g., smooth outer surfaces, tapered ends, etc.) to facilitate movement past other reinforcing elements and/or intervening structures (e.g., catheter structures). Furthermore, where the one or more reinforcing elements comprise flexible reinforcing sheets (e.g., concentric tubes or rolled sheets) which are intended to be radially compressed during delivery to facilitate passage through a small opening (e.g., a catheter or surgical opening), the flexible reinforcing sheets (e.g., concentric tubes or rolled sheets) may comprise resilient elements (e.g., resilient rings) to assist their subsequent return to an expanded state when positioned within the containment bag.

The filaments and particulates used to form the aforementioned reinforcing elements may be biodegradable or bioabsorbable, or non-biodegradable or non-bioabsorbable. By way of example but not limitation, suitable biodegradable or bioabsorbable materials include polyglycolide (PGA), glycolide copolymers, glycolide/lactide copolymers (PGA/PLA), glycolide/trimethylene carbonate copolymers (PGA/TMC), stereoisomers and copolymers of polylactide, poly-L-lactide (PLLA), poly-D-lactide (PDLA), poly-DL-lactide (PDLLA), L-lactide, DL-lactide copolymers, L-lactide, D-lactide copolymers, lactide tetramethylene glycolide copolymers, lactide/trimethylene carbonate copolymers, lactide/delta-valerolactone copolymers, lactide/epsilon-caprolactone copolymers, polydepsipeptide (glycine-DL-lactide copolymer), polylactide/ethylene oxide copolymers, asymmetrically 3,6-substituted poly-1,4-dioxane-2,4-diones, poly-β hydroxybutyrate (PHBA), PHBA/beta-hydroxyvalerate copolymers (PHBA/PHVA), poly-beta.-hydroxypropionate (PHPA), poly-beta-dioxanone (PDS), poly-DELTA-valerolactone, poly-DELTA-caprolactone, methyl methacrylate-N-vinyl pyrrolidone copolymers, polyester amides, oxalic acid polyesters, polydihydropyrans, polypeptides from alpha-amino acids, poly-beta-maleic acid (PMLA), poly-beta-alkanoic acids, polyethylene oxide (PEO), silk, collagen, derivatized hyaluronic acid and chitin polymers, and resorbable metals, resorbable ceramics, and soluble glasses. By way of further example but not limitation, suitable non-biodegradable or non-bioabsorbable materials include polyolefins, polyamides, polyesters and polyimides, polyetheretherketone (PEEK), and carbon fiber, and metals, ceramics, and glasses.

As will hereinafter be discussed, the one or more reinforcing elements 15 are selected by the physician so as to provide the composite implant with the desired size, stiffness and strength. Thus, and as will hereinafter be discussed, the physician may select from a variety of different reinforcing elements, each having a particular composition and length, and preferably deliver those reinforcing elements sequentially to the patient, whereby to provide the composite implant with the desired size, stiffness and strength. The physician may, optionally, size the reinforcement elements to the appropriate length.

The injectable matrix material is preferably polymeric and is preferably biodegradable. The matrix material is preferably a multi-component polymer system that is mixed immediately prior to introduction into the patient. Optionally, the injectable matrix material may contain a biocompatible solvent, with the solvent reducing viscosity so as to allow the matrix material to be injected, and with the solvent thereafter rapidly diffusing from the composite implant so as to facilitate or provide stiffening of the composite implant. The solvent may also be used to alter the porosity of the injectable matrix material.

In one preferred form of the invention, the injectable matrix material is preferably an organic polymer that can be formed via a polymerization process.

If desired, the injectable matrix material may also comprise a bioactive filler material, a therapeutic agent, and/or an agent to enhance visibility while imaging the composite implant.

The composite implant is disposed within the intramedullary canal of a bone, or within another opening in the bone, so as to function as an internal "splint", whereby to carry the stress created during patient activity. This allows a bone fracture to heal, or provides fortification and/or augmentation of bone, with minimum inconvenience to the patient. The components of the composite implant are introduced sequentially into the patient, and assembled in-situ, thereby allowing the composite implant to be installed using a minimally invasive approach.

By way of example but not limitation, the composite implant may be used in the following manner to treat a fracture in the tibia.

The first step is to create an access hole into the bone that is to be treated. When treating fractures in long bones, the hole is made into the intramedullary canal distal to, or proximal to, the fracture site.

The second step is to remove or harvest the bone marrow (and/or other matter) in the intramedullary canal, and to clean the intramedullary canal, so as to provide a space for the composite implant. This is done through the access hole previously created. In one preferred form of the invention, the device for removing or harvesting of the bone marrow from the intramedullary canal comprises a catheter with provision for introducing a liquid or gas into the intramedullary canal and suction for removal of material from the intramedullary canal. The liquid or gas can be used to disrupt the content in the intramedullary canal or prepare the intramedullary canal for a composite implant. The liquid or gas can be introduced in a continuous, pulsed, or intermittent flow. A rotatable flexible rod, with a shaped end or attachment at the distal end, is optionally used to disrupt the bone marrow in the intramedullary canal so as to aid in the removal of the bone marrow. When harvest of the bone marrow is required, a tissue trap is utilized.

The third step, if needed, is to place a flow restrictor plug in the intramedullary canal distal to, and/or proximal to, where the composite implant will be placed in the intramedullary canal. Again, this is done through the access hole previously created. The flow restrictor plugs may be placed prior to the removal or harvest of the bone marrow (and/or other matter) to define the area to be cleaned. Where two flow restrictor plugs are used, the two flow restrictor plugs may be connected to one another.

The fourth step, if needed, is to return the bone to proper alignment.

The fifth step is to introduce the containment bag into the intramedullary canal via the access hole previously created. In one preferred form of the invention, the containment bag is introduced into the intramedullary canal through a delivery catheter, and is releasably attached to a catheter that is used for subsequent delivery of the remaining components of the composite implant, i.e., the one or more reinforcement elements and the injectable matrix material. Note that the flexible (and compressible) nature of the containment bag facilitates its delivery into the intramedullary canal via a minimally invasive approach (i.e., via the access hole previously created). The containment bag may comprise an auxiliary channel to allow monitoring and control of subsequent pressure within the containment bag. The auxiliary channel may be used to remove entrapped air from the composite implant during filling of the containment bag with the injectable matrix material. The auxiliary channel may also be used to pressurize the injectable matrix material so as to enhance bonding of the injectable matrix material with adjacent structures (e.g., the reinforcing elements, the containment bag, bone, etc.). This auxiliary channel may be parallel to the delivery catheter, or inside the delivery catheter, or the auxiliary channel may be at the distal end of the containment bag. Alternatively, there may be a valve at the distal end of the containment bag, or at other strategic regions of the containment bag, that can limit pressure within the containment bag.

The sixth step is to sequentially introduce the one or more reinforcing elements into the containment bag. This is done through the access hole previously created. Note that the flexible nature of the reinforcing elements facilitates their delivery into the containment bag via the access hole previously created. The one or more reinforcing structures are preferably introduced into the containment bag sequentially so as to build up a reinforcing mass. In one preferred form of the invention, a plurality of flexible concentric reinforcing tubes are sequentially inserted into the containment bag, with one flexible reinforcing tube being nested inside another, and a plurality of flexible reinforcing rods are sequentially inserted within the innermost concentric reinforcing tube. In one preferred form of the invention, the flexible reinforcing sheets (which are preferably in the form of concentric tubes or rolled sheets) are delivered to the interior of the containment bag by pushing them out of a delivery tube or, alternatively, by carrying them into the containment bag while held within a delivery tube and then retracting the delivery tube, whereby to expose the flexible reinforcing sheets. Preferably the size and number of concentric reinforcing tubes and reinforcing rods are selected so as to meet the individual needs of a particular patient. The number of concentric reinforcing tubes utilized in the composite implant, and/or their lengths and/or cross-sectional dimensions, and/or the number of reinforcing rods used, and/or their lengths and/or cross-sectional dimensions, may be selected according to the individual needs of a particular patient. Preferably the number, length, and cross-sectional dimensions of the reinforcing tubes, and the number, length, and cross-sectional dimensions of the reinforcing rods, are selected so as to provide a composite implant having variable stiffness along its length, e.g., a composite implant having a stiffer central region (e.g., 20 GPa) and less stiff distal and proximal ends (e.g., 3 GPa), whereby to prevent stress risers from being created at the ends of the composite implant. To this end, the reinforcing tubes, and the reinforcing rods, are preferably provided in a variety of sizes with a range of mechanical properties for appropriate selection by the physician; alternatively, the reinforcing tubes and/or reinforcing rods may be sized at the time of use by the physician. If desired, a guidewire may be provided to facilitate introduction of the one or more reinforcing elements into the containment bag. This guidewire is preferably attached to the distal end of the containment bag using an adhesive or other non-permanent attachment means. After the one or more reinforcement elements have been placed in the containment bag, the guidewire can be detached from the containment bag by pulling or twisting the guidewire. Alternatively, the guidewire may be absorbable, in which case it may be left in the patient at the conclusion of the procedure.

The seventh step is to introduce the injectable matrix material into the containment bag. Again this is done through the access hole previously created. In one preferred form of the invention, an injection tube is used to deliver the injectable matrix material into the containment bag under pressure, where it flows over and through the one or more reinforcement structures contained within the containment bag. Suction may be used during the delivery of the injectable matrix material to aid in the wetting out of the reinforcement structures and removal of trapped air. The injection tube is withdrawn after the matrix material is injected into the containment bag. The injection tube is, preferably, also capable of transmitting an energy wave into the injectable matrix material in cases where pulsatile flow or the application of vibrational forces is required to aid injecting the matrix material into the containment bag.

The eighth step is to solidify the injectable matrix material so that the matrix material, the one or more reinforcing elements and the containment bag become a single solidified structure capable of providing support across the fracture line while the bone fracture heals.

The ninth step is to close the wound.

Thus it will be seen that the present invention comprises the provision and use of a novel composite implant for treating bone fractures (and/or for fortifying and augmenting a bone). The composite implant is disposed within the intramedullary canal of the bone (or within another opening in the bone) so as to function as a "splint", whereby to carry the stress created during patient activity. This approach allows the bone fracture to heal (or provides fortification and/or augmentation of a bone) with minimum inconvenience to the patient. The composite implant comprises a plurality of components that are introduced sequentially into the patient, and assembled in situ, thereby allowing the composite implant to be installed using a minimally invasive approach. Significantly, the properties of the composite implant can be custom tailored for different treatment situations, e.g., the composite implant can have different lengths and/or cross-sectional dimensions, the composite implant can have different mechanical properties, e.g. compressive and/or tensile strengths, etc., all according to the individual needs of a particular patient.

In one preferred form of the present invention, there is provided a composite implant comprising an injectable matrix material which is flowable and settable, and at least one reinforcing element for integration with the injectable matrix material, the at least one reinforcing element adding sufficient strength to the injectable matrix material such that when the composite implant is disposed in a cavity in a bone, the composite implant supports the bone.

In another preferred form of the present invention, there is provided a method for treating a bone, the method comprising:

selecting at least one reinforcing element to be combined with an injectable matrix material so as to together form a composite implant capable of supporting the bone;

positioning the at least one reinforcing element in a cavity in the bone;

flowing the injectable matrix material into the cavity in the bone so that the injectable matrix material interfaces with the at least one reinforcing element; and transforming the injectable matrix material from a flowable state to a non-flowable state so as to establish a static structure for the composite implant, such that the composite implant supports the adjacent bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 8A, 8B, 8C and 8D are schematic views showing alternative forms of the flexible reinforcing rods of the present invention;

DETAILED DESCRIPTION OF THE PREFERRED EMBODIMENTS

The present invention provides a new approach for treating bone fractures.

The present invention also provides a new approach for fortifying and/or augmenting a bone.

Composite Implant

More particularly, the present invention comprises the provision and use of a novel composite implant for treating bone fractures and/or for fortifying and/or augmenting a bone. The composite implant is disposed within the intramedullary canal of a bone, or within another opening in the bone, so as to function as an internal "splint", whereby to carry the stress created during patient activity. This allows a bone fracture to heal, or provides fortification and/or augmentation of a bone, with minimum inconvenience to the patient. The composite implant comprises a plurality of components that are introduced sequentially into the patient, and assembled in-situ, wherein each of the components has a size and flexibility that allows it to be installed using a minimally invasive approach while collectively providing the required structural reinforcement for the bone that is being treated. Significantly, the properties of the composite implant can be custom tailored for different treatment situations, e.g., the composite implant can have different lengths and/or different cross-sectional dimensions, the composite implant can have different compressive and/or tensile strengths, etc., all according to the individual needs of a particular patient.

Figure 1:
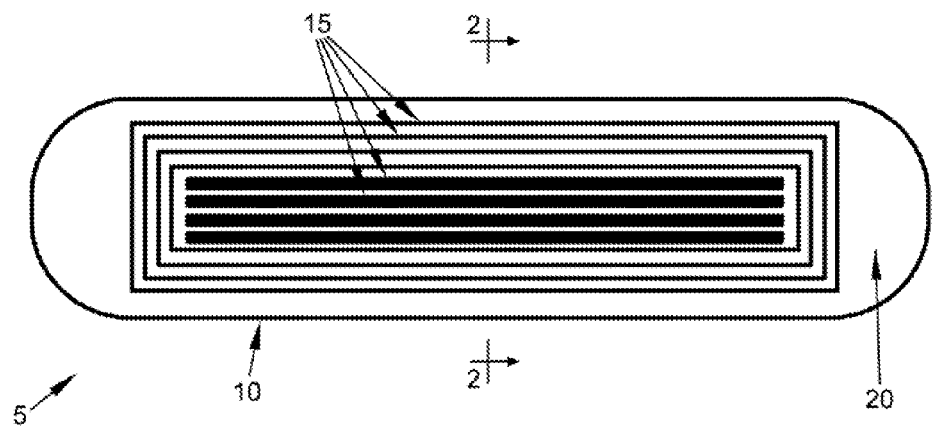
FIGS. 1 and 2 are schematic views of a composite implant formed in accordance with the present invention.
Figure 2:
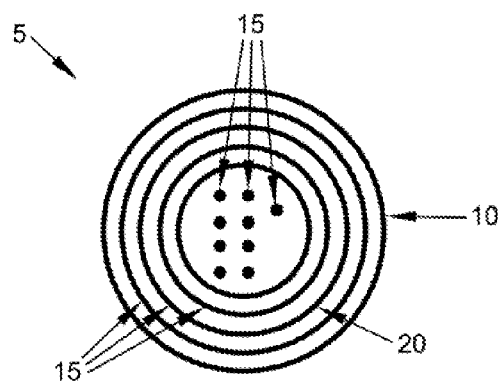

In one preferred form of the invention, and looking now at FIGS. 1 and 2, the composite implant 5 comprises three components: a containment bag 10, one or more reinforcing elements 15 and an injectable matrix material 20.

Containment Bag

The containment bag 10 serves to protect the remaining components of the composite implant from the ingress of blood and/or other bodily fluids that might interfere with the deployment of the one or more reinforcing elements 15 and/or interfere with the deployment or solidification of the injectable matrix material 20. The containment bag 10 also serves to constrain the flow of the injectable matrix material 20 while the injectable matrix material 20 is in its injectable state. The containment bag is flexible and may be fabricated from a resorbable polymer such as a polyurethane, polylactic acid, glycolic acid or some mixture/copolymer thereof. Alternatively, the containment bag 10 may be formed from fibers that are woven, braided, knit, nonwoven, and/or otherwise worked so as to form a mesh bag. Suitable fibers include polylactic acid, polyglycolic acid, polydioxanone or mixtures/copolymers thereof, bioresorbable and soluble glasses, and/or metal. In any case, the containment bag preferably has sufficient strength to allow the injectable matrix material to be injected into the containment bag under substantial pressure so as to ensure good interfacial contact between the injectable matrix material and the one or more reinforcing elements, the containment bag and the bone, and to minimize voids within the containment bag. Ideally the mesh bag is hydrophobic so as to minimize the ingress of bodily fluids into the containment bag that may otherwise interfere with the deployment or solidification or accelerate the degradation of the various components of the composite implant. Optionally, the mesh bag may have a limited porosity to allow some egress of the injectable matrix material 20 out of the containment bag, e.g., to osseointegrate with the surrounding bone. In this respect it should be appreciated that such porosity may be varied across the extent of the containment bag so as to provide regions of greater or lesser porosity to the injectable matrix material 20, thus providing control of the ability of the injectable matrix material to infiltrate the surrounding bone.

Reinforcing Elements

Figure 3:
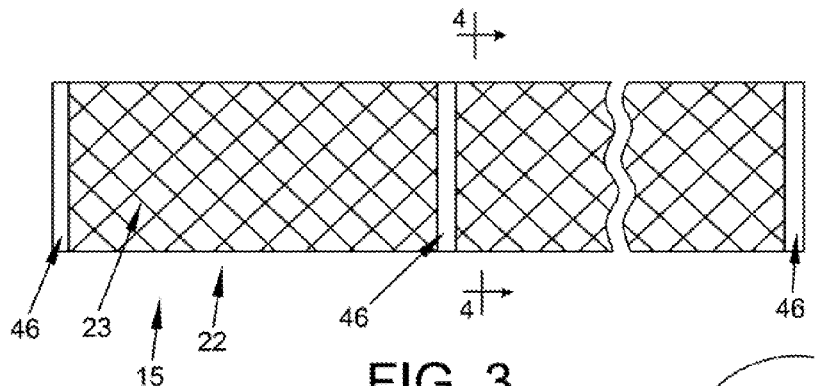
FIGS. 3 and 4 are schematic views of a concentric reinforcing tube that may be used to form the composite implant of FIGS. 1 and 2.
Figure 4:
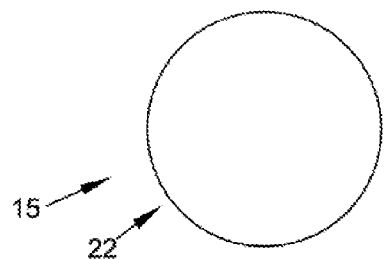
Figure 5:
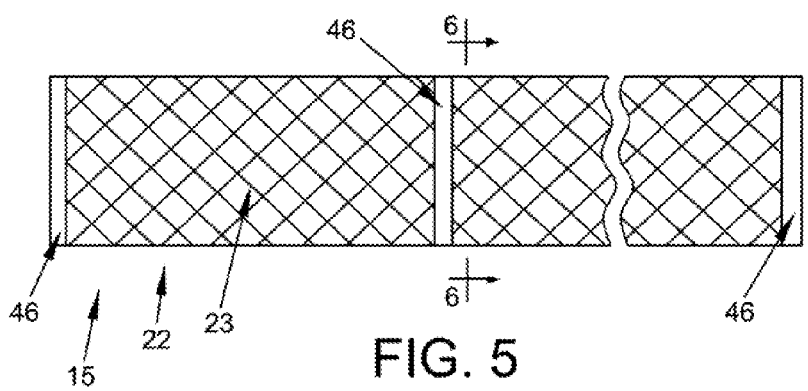
FIGS. 5 and 6 are schematic views of a rolled sheet that may be used to form the composite implant of FIGS. 1 and 2.
Figure 6:
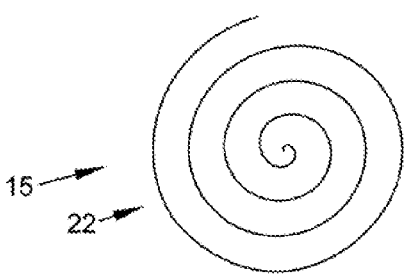
Figures 6A, 6B:
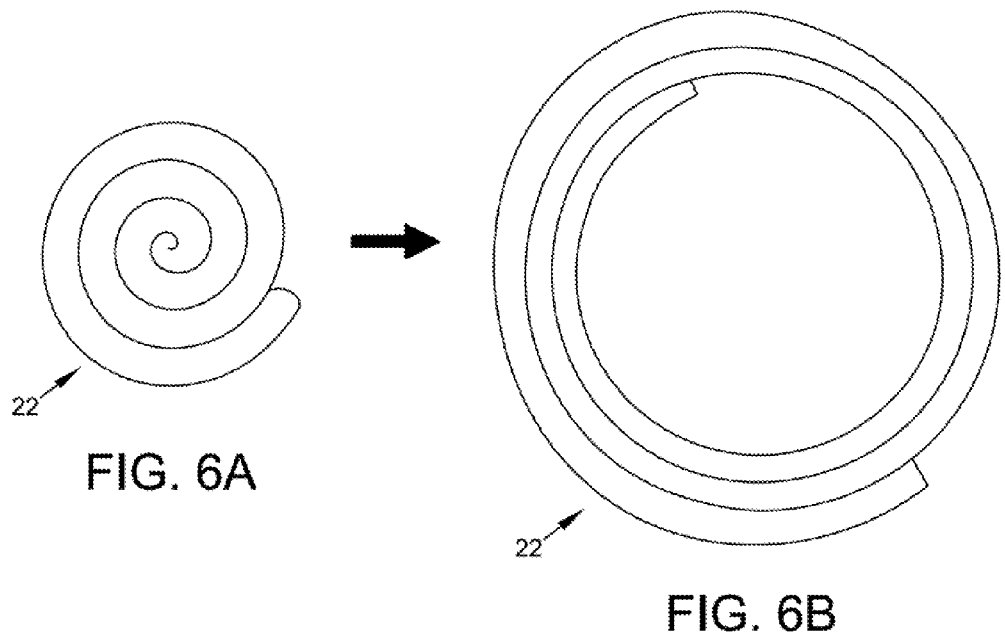
FIGS. 6A and 6B are schematic views showing how a flexible rolled reinforcing sheet may be radially compressed during delivery to the containment bag (FIG. 6A) and thereafter radially expanded (FIG. 6B) within the containment bag.
Figure 7:
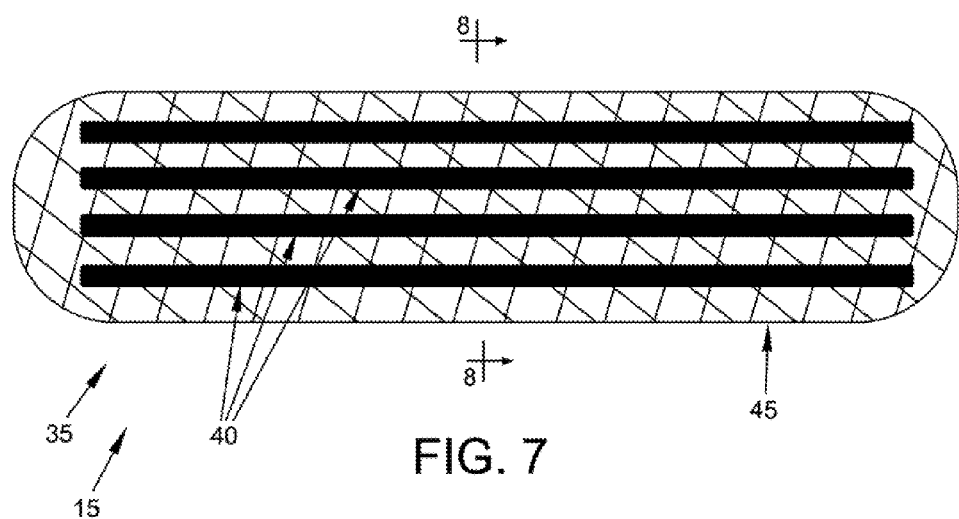
FIGS. 7 and 8 are schematic views of a flexible reinforcing rod that may be used to form the composite implant of FIGS. 1 and 2.
Figure 8:
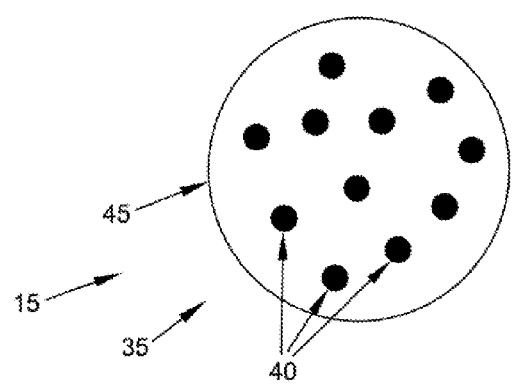
Figure 8C:
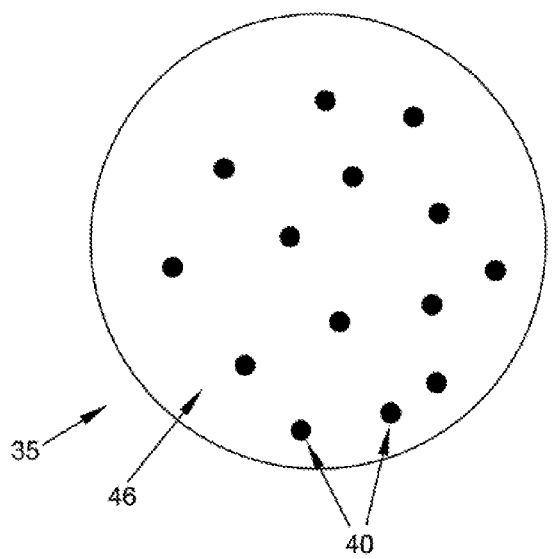
Figure 8D:
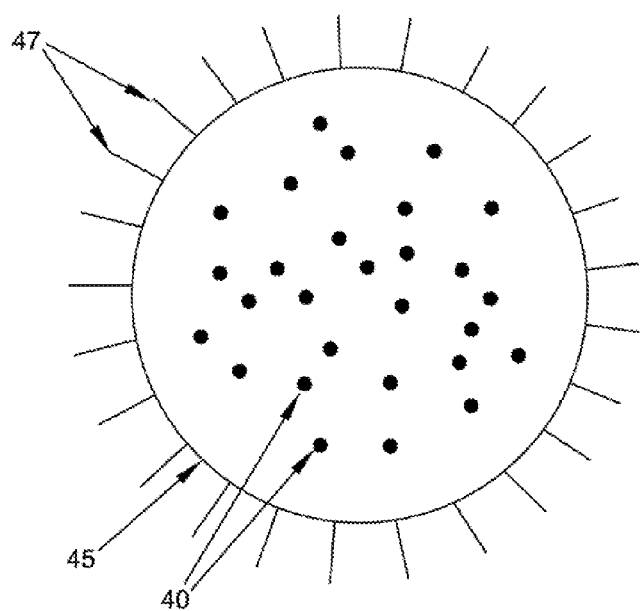

The one or more reinforcing elements 15 comprise (i) flexible reinforcing sheets 22 (which are preferably in the form of concentric tubes such as is shown in FIGS. 3 and 4 or rolled sheets such as is shown in FIGS. 5 and 6, the flexible reinforcing sheet having an arcuate cross-section or the flexible reinforcing sheet having a planar cross-section), with the flexible reinforcing sheets 22 comprising filaments 23 formed into a textile (i.e., woven, braided, knit, nonwoven, and/or otherwise worked so as to form the flexible reinforcing sheets 22) or incorporated into a film so as to form the flexible reinforcing sheets 22, (ii) flexible reinforcing rods 35 (FIGS. 7, 8, 8A, 8B, 8C and 8D), with the flexible reinforcing rods 35 comprising a plurality of filaments 40 which are held together by an outer sheath 45 (FIGS. 7 and 8) of a textile or film (which may or may not have the same composition and fiber orientation as the aforementioned flexible reinforcing sheets 22), or by a compacted (wound or compressed, etc.) connecting structure of a textile or film 45A (FIGS. 8A and 8B), or by a binder 46 (FIG. 8C) such as an adhesive, with or without surface projections 47 for improved integration with injectable matrix material 20, (iii) particulates (e.g., particles, granules, segments, whiskers, nanotubes, nanorods, etc.), or (iv) combinations of the foregoing. Where the one or more reinforcing elements comprise flexible reinforcing sheets and/or flexible reinforcing rods, the one or more reinforcing elements preferably have sufficient column strength to allow longitudinal delivery into the containment bag by pushing, and preferably have a configuration (e.g., textured outer surfaces, tapered ends, etc.) to facilitate movement past other reinforcing elements and/or intervening structures (e.g., catheter structures). The one or more reinforcing elements preferably can be introduced by means of a delivery catheter or sheath. Furthermore, where the one or more reinforcing elements comprise flexible reinforcing sheets (e.g., concentric tubes or rolled sheets) which are intended to be radially compressed during delivery to facilitate passage through a small opening (e.g., a catheter or surgical opening), the flexible reinforcing sheets (e.g., concentric tubes or rolled sheets) may comprise resilient elements 46 (e.g., resilient rings) to assist their subsequent return to an expanded state when positioned within the containment bag. The resilient elements may be thermosensitive or have a shape memory.

The filaments, fibers, and particulates used to form the aforementioned reinforcing elements may be biodegradable or bioabsorbable, or non-biodegradable or non-bioabsorbable. By way of example but not limitation, suitable biodegradable or bioabsorbable materials include polyglycolide (PGA), glycolide copolymers, glycolide/lactide copolymers (PGA/PLA), glycolide/trimethylene carbonate copolymers (PGA/TMC), stereoisomers and copolymers of polylactide, poly-L-lactide (PLLA), poly-D-lactide (PDLA), poly-DL-lactide (PDLLA), L-lactide, DL-lactide copolymers, L-lactide, D-lactide copolymers, lactide tetramethylene glycolide copolymers, lactide/trimethylene carbonate copolymers, lactide/delta-valerolactone copolymers, lactide/epsilon-caprolactone copolymers, polydepsipeptide (glycine-DL-lactide copolymer), polylactide/ethylene oxide copolymers, asymmetrically 3,6-substituted poly-1,4-dioxane-2,4-diones, poly-β hydroxybutyrate (PHBA), PHBA/beta-hydroxyvalerate copolymers (PHBA/PHVA), poly-beta.-hydroxypropionate (PHPA), poly-beta-dioxanone (PDS), poly-DELTA-valerolactone, poly-DELTA-caprolactone, methyl methacrylate-N-vinyl pyrrolidone copolymers, polyester amides, oxalic acid polyesters, polydihydropyrans, polypeptides from alpha-amino acids, poly-beta-maleic acid (PMLA), poly-beta-alkanoic acids, polyethylene oxide (PEO), silk, collagen, derivatized hyaluronic acid resorbable or soluble glasses, resorbable ceramic, resorbable metal and chitin polymers. By way of further example but not limitation, suitable non-biodegradable or non-bioabsorbable materials include polyolefins, polyamides, polyesters and polyimides, polyetheretherketone (PEEK), glass, ceramic, metal, and carbon fiber.

As will hereinafter be discussed, the one or more reinforcing elements 15 are selected by the physician so as to provide the composite implant with the desired size and mechanical properties, e.g. stiffness and strength. Thus, and as will hereinafter be discussed, the physician may select from a variety of different reinforcing elements, each having a particular composition and length, and preferably deliver those reinforcing elements sequentially to the patient, whereby to provide the composite implant with the desired size and attributes of stiffness and strength.

In one preferred form of the invention, the one or more reinforcing elements 15 comprise from about 5% to 95% (by volume) of the composite implant, typically at least 20% (by volume) of the composite implant.

In another embodiment, the reinforcing properties of the one or more reinforcing elements 15 may be modified by changing the materials, dimensions, shape, and surface characteristics of the fibers, filaments, and particulates.

In another embodiment, the reinforcing properties of the one or more reinforcing elements 15 may be modified by changing the orientation, volume, twist, and angle of the fibers and filaments within the reinforcing elements. In preferred constructions, the fibers and filaments are typically set at an acute angle to intersecting fibers and filaments in order to strengthen the reinforcing structure, but the angle may be any angle between 0 degrees and 90 degrees.

In another embodiment, the properties of the composite implant may be modified by changing the orientation of one or more of the reinforcing elements 15, and/or by changing the volume of one or more of the reinforcing elements 15.

It will be appreciated that the properties of the composite implant may be modified by changing the layup or selection of one or more of the reinforcing elements 15.

It will also be appreciated that the reinforcing properties, and degradation profiles, of the one or more reinforcing elements 15 may be modified by changing the material, dimensions, shape, orientation, volume, and surface features of the fibers, filaments, and/or particulates used to form the one or more reinforcing elements 15.

Where the reinforcement elements comprise a textile, its reinforcing properties and degradation profile may be modified by changing the materials, orientation, length, shape, volume, twist, and angle of the fibers and filaments within the textile of the reinforcing elements. The fibers and filaments in a textile of a reinforcing element are preferably set at an acute angle to intersecting fibers and filaments, but the angle may vary between 0 degrees and 90 degrees or random.

Compatibility among the specific components that comprise a composite structure is essential in order to ensure optimal interfacial bonding, mechanical properties, physical properties, and osseointegration. Compounds known as coupling agents or compatibilizers, which may be incorporated into the components of the composite implant, serve to enhance the chemical bonding between the specific components of the composite implant. In a preferred embodiment, the interfacial bond strength between the containment bag, reinforcing elements, injectable matrix material, and bone can be enhanced through the addition of a variety of compatibilizers, e.g., calcium phosphate, hydroxyapatite, calcium apatite, fused-silica, aluminum oxide, apatite-wollastonite glass, bioglass, compounds of calcium salt, phosphorus, sodium salt and silicates, maleic anhydride, diisocyanate, epoxides, silane, and cellulose esters. These agents may be incorporated into, and/or applied to, the components of the composite implant through a number of methods, e.g., plasma deposition, chemical vapor deposition, dip coating, melt-blending, spin or spray-on. A specific example is the application of a silane coupling agent to glass fiber reinforcement in order to increase its interfacial bonding strength with the injectable matrix material. Another example is the vapor deposition of calcium phosphate onto the surface of the containment bag such that the bonding between the injectable matrix material and the containment bag is enhanced. In order to increase the compatibility between the containment bag and bone that it is supporting, dip-coating the exterior of the containment bag with an osseoconductive material (such as fused-silica with aluminum oxide) will improve their adhesion to each other and accelerate osseointegration.

Those skilled in the art will recognize still other ways to modify the properties of the composite implant in view of the present disclosure.

Injectable Matrix Material

The injectable matrix material 20 is preferably polymeric and is preferably biodegradable. The injectable matrix material 20 is designed to be polymerized in situ. The matrix material is preferably a multi-component polymer system that is mixed immediately prior to introduction into the patient. Optionally, the injectable matrix material 20 may contain a biocompatible solvent, with the solvent reducing viscosity so as to allow the matrix material to be injected, and with the solvent thereafter rapidly diffusing from the composite implant so as to facilitate or provide stiffening of the composite implant 5. The solvent may also be used to alter the porosity of the injectable matrix material 20.

In a preferred embodiment of the present invention, polyurethanes are utilized as the injectable matrix material, although other suitable chemistry systems will be apparent to those skilled in the art. The polyurethanes are produced through the reaction of a difunctional or multifunctional isocyanate with a difunctional or multifunctional compound containing an active hydrogen, including water, hydroxyl materials and amines.

Suitable isocyanates useful in the practice of this invention include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, dimethyl diisocyanate, lysine diisocyanate, 2-methylpentane-1, 5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate.

The present invention comprises the use of these same multi-functional isocyanates with multifunctional amines or multifunctional substituted amines, multifunctional ketimines, multifunctional aldimines, isocyanurates or biurets. By way of example but not limitation, such multifunctional amines may include hexamethylene diamine, isophorone diamine, and lysine. Examples of substituted amines may include N-substituted diaspartic acid derivatives. Examples of multifunctional ketimines and aldimines may be made from the multifunctional amines mentioned previously and methyl isobutyl ketone or isobutyraldehyde.

When a non-biodegradable implant is desired, the aromatic isocyanates are generally favored. When a biodegradable implant is desired, the aliphatic isocyanates are generally favored. In an embodiment of this invention, the aliphatic isocyanates are preferred.

In a preferred embodiment of this invention, the isocyanate component is reacted with a polyol to produce a polyurethane. Suitable polyols include, but not limited to, polycaprolactone diol and polycaprolactone triol. Suitable dihydroxy compounds which may be utilized in the practice of this invention include, but are not limited to, ethylene glycol, propylene glycol, butylene glycol, hexylene glycol and polyols including polyalkylene oxides, polyvinyl alcohols, and the like. In some embodiments, the polyol compounds can be a polyalkylene oxide such as polyethylene oxide ("PEO"), polypropylene oxide ("PPO"), block or random copolymers of polyethylene oxide (PEO) and polypropylene oxide (PPO). Higher functional polyol compounds are also useful and can include glycerin, 1,2,4-butanetriol, trimethylol propane, pentaerythritol and dipentaerythritol, 1,1,4,4-tetrakis(hydroxymethyl)cyclohexane. Other useful polyols can include triethanol amine and N,N,N',N'-Tetrakis(2-hydroxyethyl) ethylenediamine.

The polyol materials discussed above may be used alone or, optionally, as mixtures thereof. The foregoing materials are merely examples of useful components for producing polyurethanes and should not be viewed as a limitation of the present invention. These higher functional polyol materials will produce highly crosslinked polyurethanes with high hardness and stiffness.

In preferred embodiments, the multifunctional hydroxyl material may include at least one bioabsorbable group to alter the degradation profile of the resulting branched, functionalized compound. Bioabsorbable groups which may be combined with the multifunctional compound include, but are not limited to, groups derived from glycolide, glycolic acid, lactide, lactic acid, caprolactone, dioxanone, trimethylene carbonate, and combinations thereof. For example, in one embodiment, the multifunctional compound may include trimethylol propane in combination with dioxanone and glycolide. Methods for adding bioabsorbable groups to a multifunctional compound are known in the art. Where the multifunctional compound is modified to include bioabsorbable groups, the bioabsorbable groups may be present in an amount ranging from about 50 percent to about 95 percent of the combined weight of the multifunctional compound and bioabsorbable groups, typically from about 7 percent to about 90 percent of the combined weight of the multifunctional compound and bioabsorbable groups.

The multifunctional compound can have a weight (average molecular weight) ranging from about 50 to about 50000, typically from about 100 to about 3000, and typically possesses a functionality ranging from about 2 to about 6.

In a preferred embodiment, the polycaprolactone diols and triols provide polyurethanes that are biodegradable.

The isocyanate is reacted with a polyol to produce a prepolymer. Methods for endcapping the polyol with an isocyanate are known to those skilled in the art. For example, a polycaprolactone diol may be combined with isophorone diisocyanate by heating to a suitable temperature ranging from about 55 degrees C. to about 80 degrees C., typically about 70 degrees C. The resulting diisocyanate-functional compound may then be stored until combined with additional polyol to form the final polyurethane product.

Reaction of the urethane prepolymer with polyol to form the final polyurethane product generally requires a catalyst to provide convenient working and cure times. Polyurethane catalysts can be classified into two broad categories, amine compounds and organometallic complexes. They can be further classified as to their specificity, balance, and relative power or efficiency. Traditional amine catalysts have been tertiary amines such as triethylenediamine (TEDA, also known as 1,4-diazabicyclo[2.2.2]octane or DABCO, an Air Products's trademark), dimethylcyclohexylamine (DM-CHA), and dimethylethanolamine (DMEA). Tertiary amine catalysts are selected based on whether they drive the urethane (polyol+isocyanate, or gel) reaction, the urea (water+isocyanate, or blow) reaction, or the isocyanate trimerization reaction (e.g., using potassium acetate, to form isocyanurate ring structure). Since most tertiary amine catalysts will drive all three reactions to some extent, they are also selected based on how much they favor one reaction over another.

Another useful class of polyurethane catalysts are the organometallic compounds based on mercury, lead, tin (dibutyl tin dilaurate), bismuth (bismuth octanoate), titanium complexes and zinc. Dibutyl tin dilaurate is a widely used catalyst in many polyurethane formulations. Stannous octoate is another catalyst that may be used.

In the practice of this invention dibutyl tin dilaurate is a favored catalyst at concentrations below 0.5% and more preferably at concentrations below 0.2% by weight.

Additions to Injectable Matrix Material

If desired, the injectable matrix material 20 may also comprise a bioactive filler material, a therapeutic agent, and/or an agent to enhance visibility while imaging the composite implant.

Fillers.

The injectable matrix material may include a filler in the form of biocompatible and or osteoconductive particles. The first or primary filler, preferably in the form of particles, may also provide porosity, bone ingrowth surfaces and enhanced permeability or pore connectivity. One suitable particulate filler material is tricalcium phosphate, although other suitable filler materials will be apparent to those skilled in the art such as orthophosphates, monocalcium phosphates, dicalcium phosphates, tricalcium phosphates, tetracalcium phosphates, amorphous calcium phosphates and combinations thereof. Also biodegradable glasses can be utilized as a filler.

The filler particles may comprise a degradable polymer such as polylactic acid, polyglycolic acid, polycaprolactone and co-polymers thereof. The particles may also comprise degradable polymer containing one or more inorganic fillers.

In one embodiment the inorganic filler particles have mean diameters ranging from about 1 micron to about 20 microns.

In another embodiment the porosity and compressive properties of the matrix material may be modified by using additional fillers that may be inorganic, organic or another suitable biocompatible material. Such refinements include the addition of particles having mean diameters ranging from about 10 microns to about 500 microns or a mean diameter of less than 1 micron. In certain matrix materials the additional filler materials may be provided in one or more size distributions.

The composite implant can become porous after implantation so as to aid the resorption and bone healing process. This porosity can be generated by various mechanisms including the preferential resorption of filler, such as calcium sulfate or α-tricalcium phosphate, bioglass or of a polymeric component. Alternatively, the formulation can include a biocompatible solvent such as DMSO that is leached out of the implant post implantation. The pores are preferably 100 μm in diameter with interconnectivity to allow bone ingrowth.

The composite implant may also include an additional porogen. In one form of the invention, the porogen is sugar or a polysaccharide, such as dextran, but other biocompatible porogens will be apparent to those skilled in the art such as crystalline materials in the form of soluble salts.

In another embodiment of the present invention, the filler, either inorganic or polymeric, may be present in combined amount ranging from about 10 to about 50 wt % of the matrix composition. In certain cases it may be desirable to have the filler content over 50 wt %. If a porogen is added, it will preferably be present in an amount ranging from about 15 to about 50 wt %.

Compatibilizing agents may also be included.

Therapeutics Agents.

The inclusion of a therapeutic agent in the injectable matrix material, or in one or more of the reinforcing elements, is contemplated in the practice of this invention. Therapeutic agents can include agents that promote bone formation, or for relief of pain. Agents may include, but are not limited to, parathyroid hormone, vitamin D, calcitonin, calcium, PO4, non-steroidal anti-inflammatory drugs (NSAIDS) such as, but not limited to, acetaminophen, salicylates (aspirin, diflunisal, salsalate), acetic acid derivatives (indomethacin, ketorolac, sulindac etodolac, diclofenac, nabumetone), propionic acid derivatives (ibuprofen, naproxen, flurbiprofen, ketoprofen, oxaprozin, fenoprofen, loxoprofen), fenamic acid derivatives (meclofenamic acid, mefenamic acid, flufenamic acid, tolfenamic acid), oxicam (enolic acid) derivatives (piroxicam, meloxicam, tenoxicam, droxicam, lornoxicam, isoxicam), arylalkanoic acid derivatives (tolmetin); selective COX-2 inhibitors (celecoxib, rofecoxib, valdecoxib, parecoxib, lumiracoxib, etoricoxib, firocoxib); steroids such as, but not limited to, corticosteroids (hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, dexamethasone, fluocortolone, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, or fluprednidene acetate); immune selective anti-inflammatory derivatives (ImSAIDs) such as, but not limited to, submandibular gland peptide T (SGp-T) and derivatives phenylalanine-glutamine-glycine (FEG) and its D-isomeric form (feG); narcotic compositions such as, but not limited to, buprenorphine, butorphanol, codeine, hydrocodone, hydromorphone, levorphail, meperidine, methadone, morphine, nalbuphine, oxycodone, oxymorphone, pentaxocine, or propoxyphene; other analgesic compositions such as, but not limited to, tramadol, or capsaicin; local anethetics (including short term acting anesthetics) such as, but not limited to, benzocaine, dibucaine, lidocaine, or prilocaine; bisphosphonates, or combinations of any of the above.

Therapeutic agents delivered locally can use a carrier vehicle to provide a protective environment, provide target delivery to cells or within cells, provide locally delivery, timed delivery, staged delivery and/or use delivery technology know in the art.

The therapeutic agents can also include bone growth activating factors, such as bone morphogenetic proteins (BMPs), FGF (fibroblast growth factor), VEGF (vascular endothelial growth factor), PDGF (platelet derived growth factor), or PGE2 (prostaglandin E2). Bone morphogenetic proteins can include BMP1, BMP2, BMP3, BMP4, BMP5, BMP6, BMP7, BMP8a, BMP8b, BMP10, or BMP15.

Agent to Enhance Visibility.

It is also possible for the injectable matrix material to include one or more particles or liquid agents to enhance visibility while imaging the composite implant. By way of example but not limitation, where the physician may be using fluoroscopy to view the bone being treated and the composite implant, the injectable matrix material may include bismuth oxychloride, bismuth subcarbonate, barium, barium sulfate, ethiodol, tantalum, titanium dioxide, tantalunipentoxide, tungsten, strontium carbonate, strontium halides platinum, titanium, silver, gold, palladium, iridium, osmium, copper, niobium, molybdenum, strontium, strontium salts and gallium, iodine substituted compounds/polymers, and/or alloys such as nickel-titanium, nickel-manganese-gallium, platinum-iridium, platinum-osmium to enhance the visibility of the injectable matrix material under fluoroscopy.

Preferred Method of Use

The composite implant 5 is disposed within the intramedullary canal of a bone, or within another opening in the bone, so as to function as an internal "splint", whereby to carry the stress created during patient activity. This allows a bone fracture to heal, or provides fortification and/or augmentation of bone, with minimum inconvenience to the patient. The components of the composite implant 5 are introduced sequentially into the patient, and assembled in-situ, thereby allowing the composite implant 5 to be installed using a minimally invasive approach.

By way of example but not limitation, the composite implant 5 may be used in the following manner to treat a fracture in the tibia.

Figure 9:
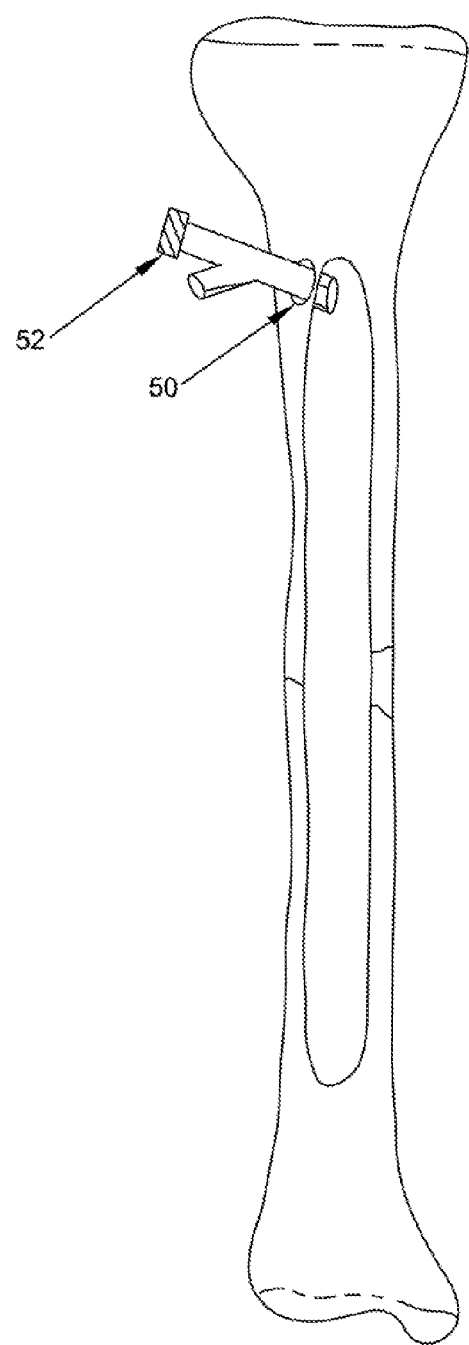
FIGS. 9-23 are schematic views showing a composite implant being assembled in situ so as to treat a bone fracture.

Looking now at FIG. 9, the first step is to create an access hole 50 into the bone that is to be treated. If desired, an access port 52 may be disposed in access hole 50 so as to facilitate delivering elements through access hole 50. When treating fractures in long bones, the hole is made into the intramedullary canal distal to, or proximal to, the fracture site. Significantly, the modular nature of the composite implant means that the composite implant can be introduced into the intramedullary canal of the bone that is to be treated through an access hole that is smaller than the final form of the composite implant. For example, in the case of where the composite implant is to fill an intramedullary canal that is 10 mm in diameter, the required access hole may be only 3 mm in diameter. As a result, the composite implant may be deployed using a minimally invasive procedure that may be carried out in an office setting or surgicenter setting rather than in a conventional operating room. Access hole 50 is preferably drilled at an acute angle to the bone which is being treated, e.g., at an angle of approximately 45 degrees, but it may be drilled at an angle anywhere between 0 degrees and 90 degrees, either proximal or distal to the fracture. This allows the components of the composite implant to be more easily introduced into the intramedullary canal.

Figure 10:
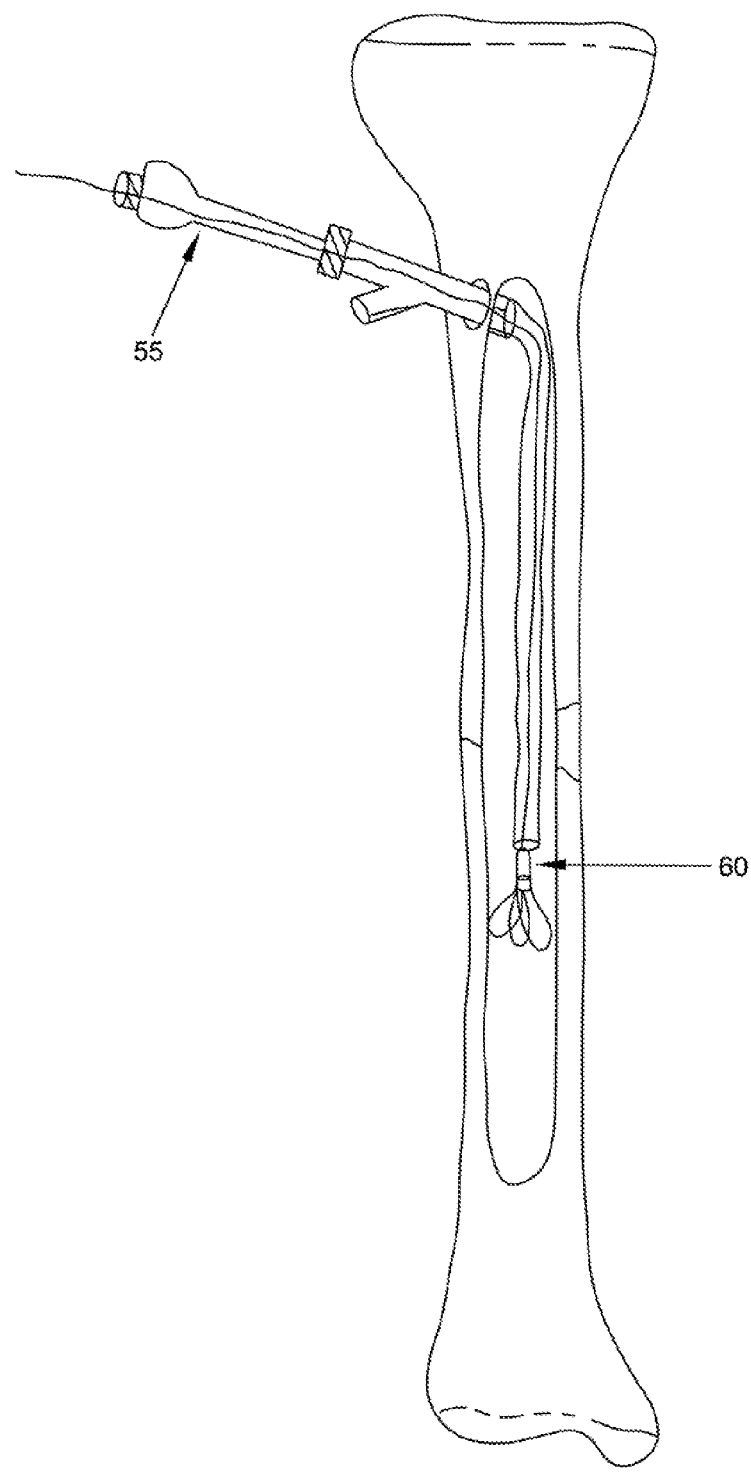
Figure 11:
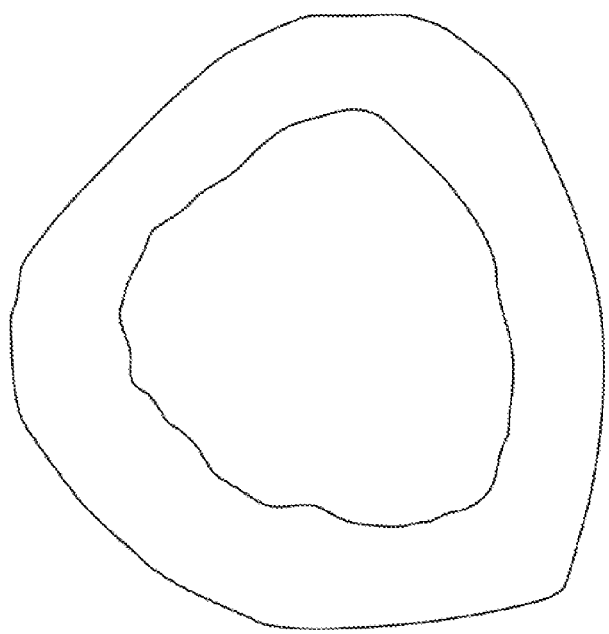

The second step is to remove or harvest the bone marrow (and/or other matter) in the intramedullary canal, and to clean the intramedullary canal, so as to provide a space for the composite implant 5. This is done through the access hole 50 previously created. In one preferred form of the invention, and looking now at FIG. 10, the device for removing or harvesting of the bone marrow from the intramedullary canal comprises a catheter 55 with provision for introducing a liquid or gas into the intramedullary canal and suction for removal of material from the intramedullary canal. The liquid or gas can be used to disrupt the content in the intramedullary canal or prepare the intramedullary canal for a composite implant. The liquid or gas can be introduced in a continuous, pulsed, or intermittent flow. A rotatable flexible rod 60, with a shaped end or attachment at the distal end (e.g., having one or more wire loops, brushes, cutting tips, etc., which may or may not be made out of a shape memory material such as Nitinol, and which may or may not be steerable), is optionally used to disrupt the bone marrow in the intramedullary canal so as to aid in the removal of the bone marrow. When harvest of the bone marrow is required, a tissue trap is utilized. FIG. 11 shows the intramedullary canal of the bone after it has been appropriately prepared.

Figure 12:
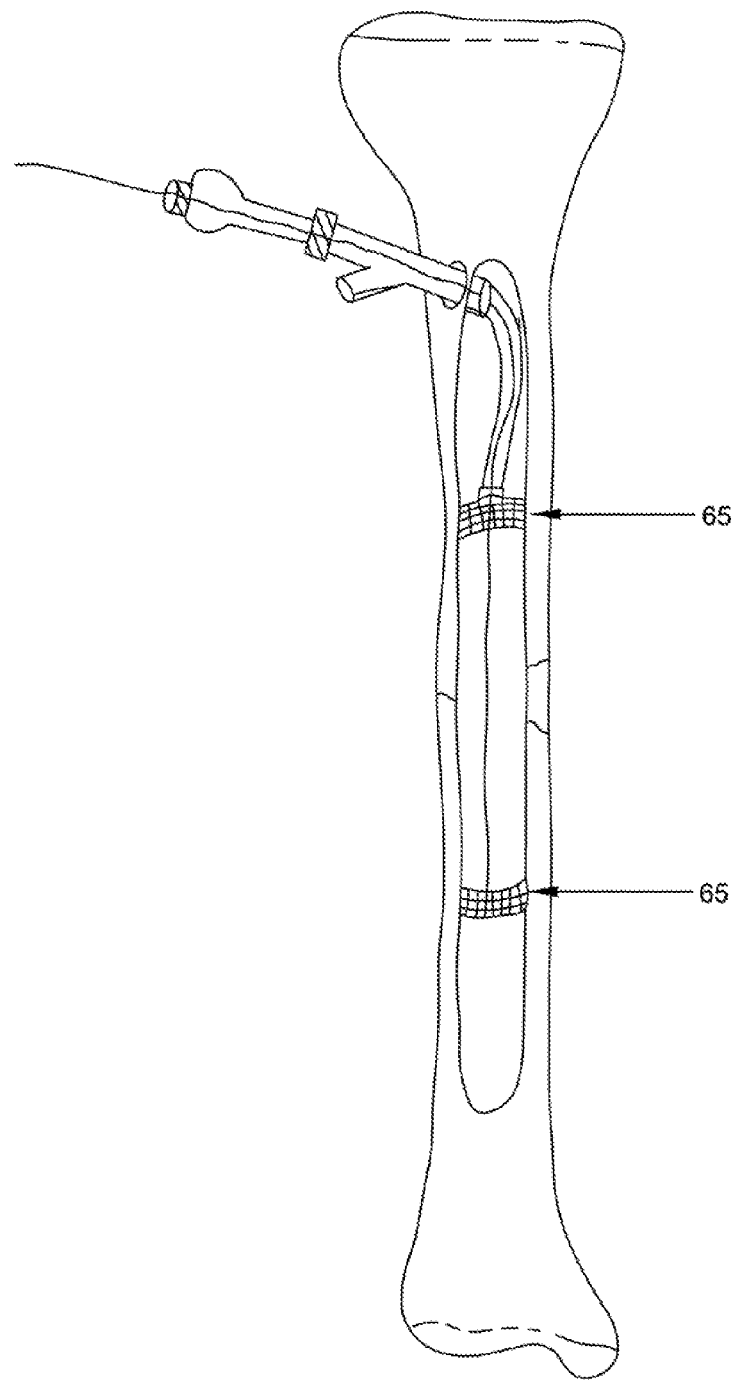

Looking next at FIG. 12, the third step, if needed, is to place a flow restrictor plug 65 in the intramedullary canal distal to, and/or proximal to, where the composite implant 5 will be placed in the intramedullary canal. Again, this is done through the access hole 50 previously created. Where two flow restrictor plugs 65 are used, the two flow restrictor plugs may be connected to one another. The flow restrictor plugs 65 may be optionally placed prior to removing or harvesting the bone marrow.

The fourth step, if needed, is to return the bone to proper alignment.

Figure 13:
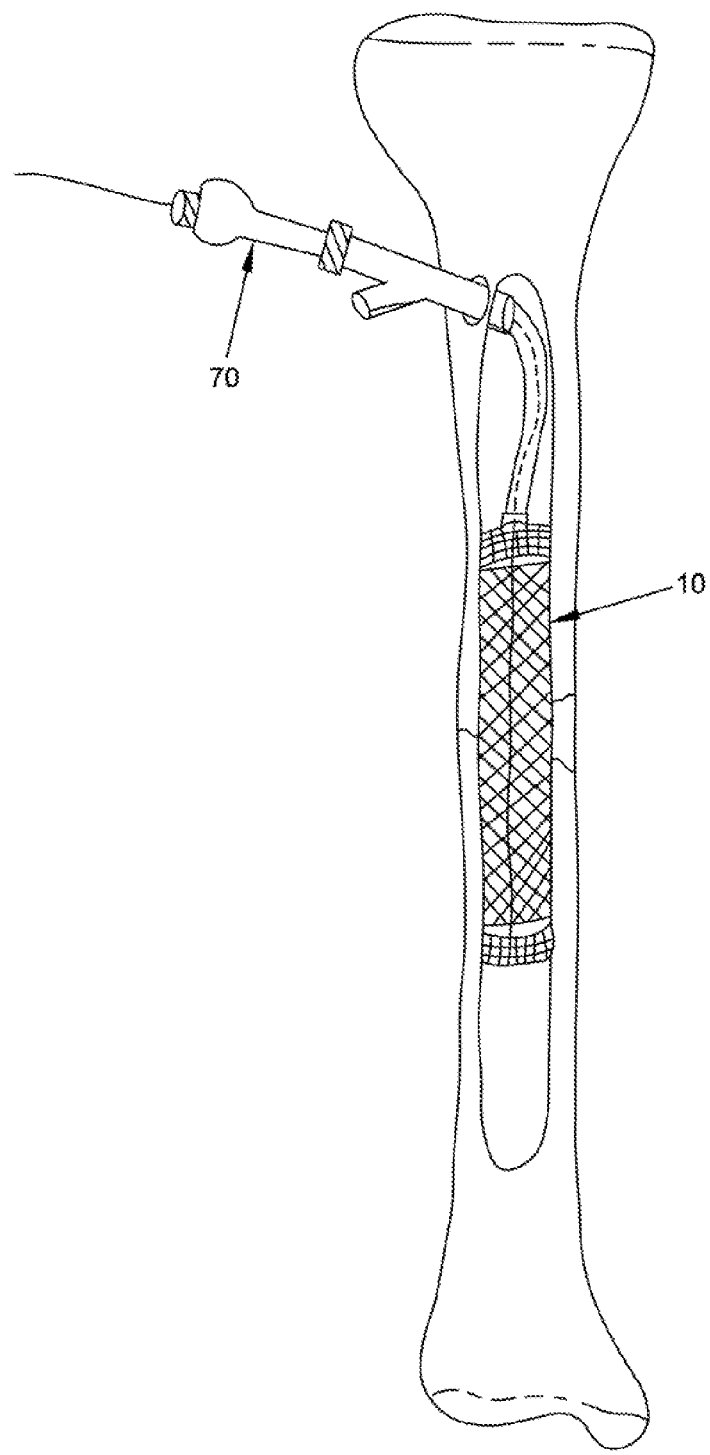
Figure 14:
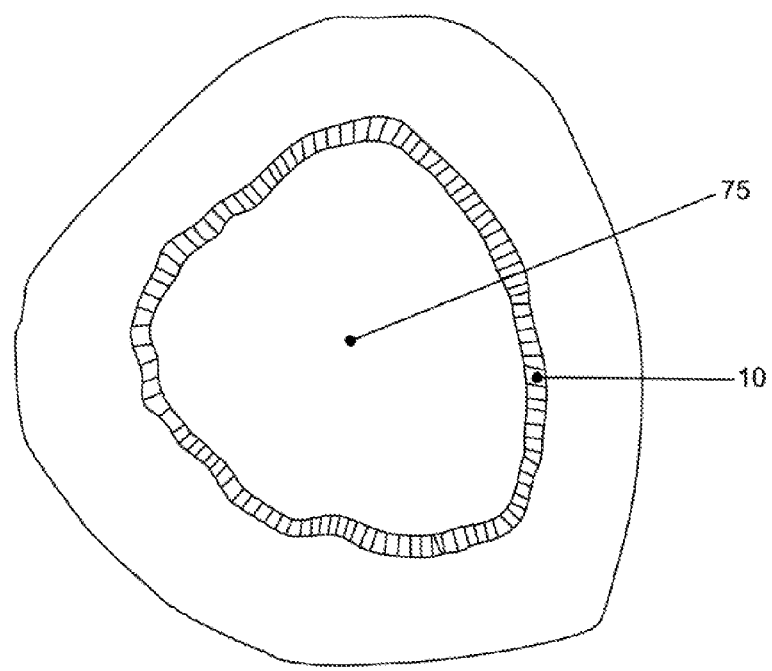

The fifth step is to introduce the containment bag 10 into the intramedullary canal via the access hole 50 previously created. In one preferred form of the invention, and looking now at FIG. 13, the containment bag 10 is introduced into the intramedullary canal through a delivery catheter 70, and is releasably attached to a catheter that is used for subsequent delivery of the remaining components of the composite implant, i.e., the one or more reinforcement elements 15 and the injectable matrix material 20. The catheter may have markers on its exterior surface so as to allow the physician to determine the position of the containment bag 10 within the bone by direct visualization of the markers on the exterior surface of the catheter. Alternatively, and/or additionally, containment bag 10 may have markers thereon so as to allow the physician to determine the position of the containment bag 10 within the bone by indirect visualization (e.g., fluoroscopy, CT, etc.). Note that the flexible (and compressible) nature of the containment bag 10 facilitates its delivery into the intramedullary canal via a minimally invasive approach (i.e., via the access hole 50 previously created). The containment bag 10 may comprise an auxiliary channel to allow monitoring and control of subsequent pressurization with the injectable matrix material. This auxiliary channel may be parallel to the delivery catheter, or inside the delivery catheter, or the auxiliary channel may be at the distal end of the containment bag. Alternatively, there may be a valve at the distal end of the containment bag, or at other strategic regions of the containment bag, that can limit pressure within the containment bag. FIG. 14 shows containment bag 10 disposed within the intramedullary canal of the bone.

Figure 15:
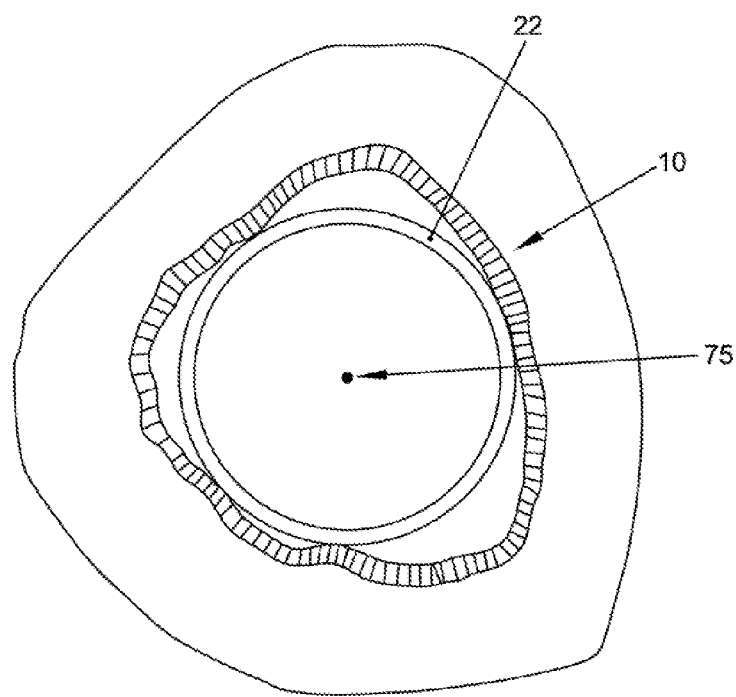
Figure 16:
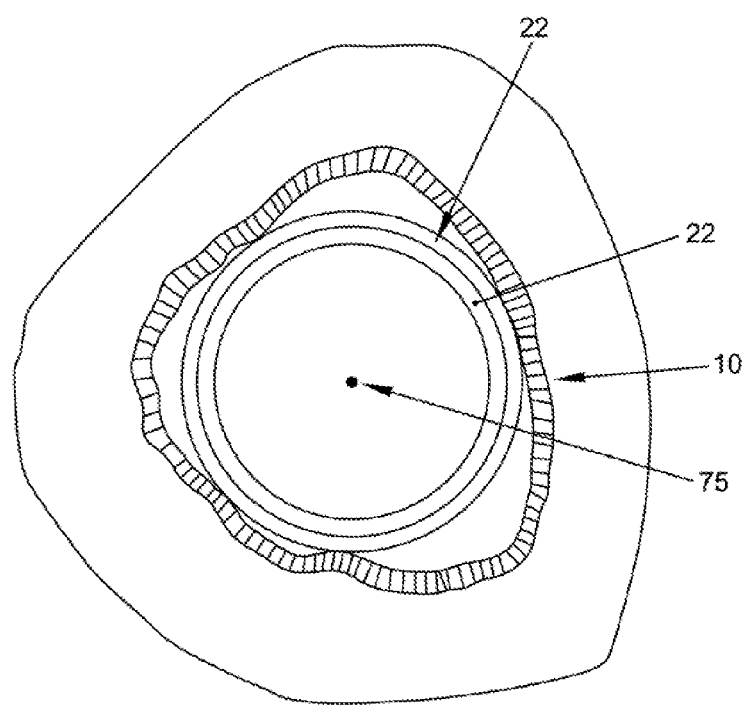
Figure 17:
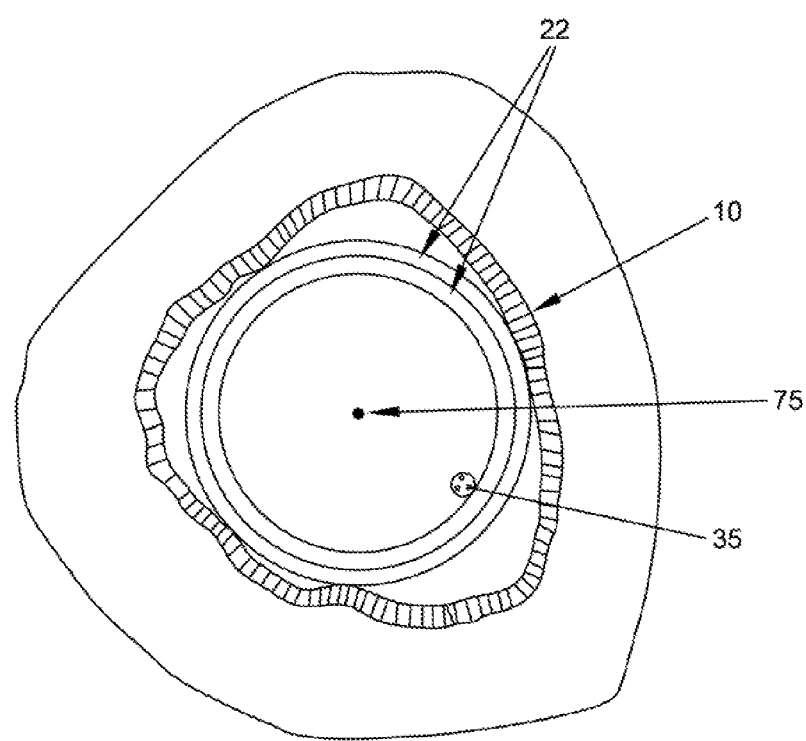
Figure 18:
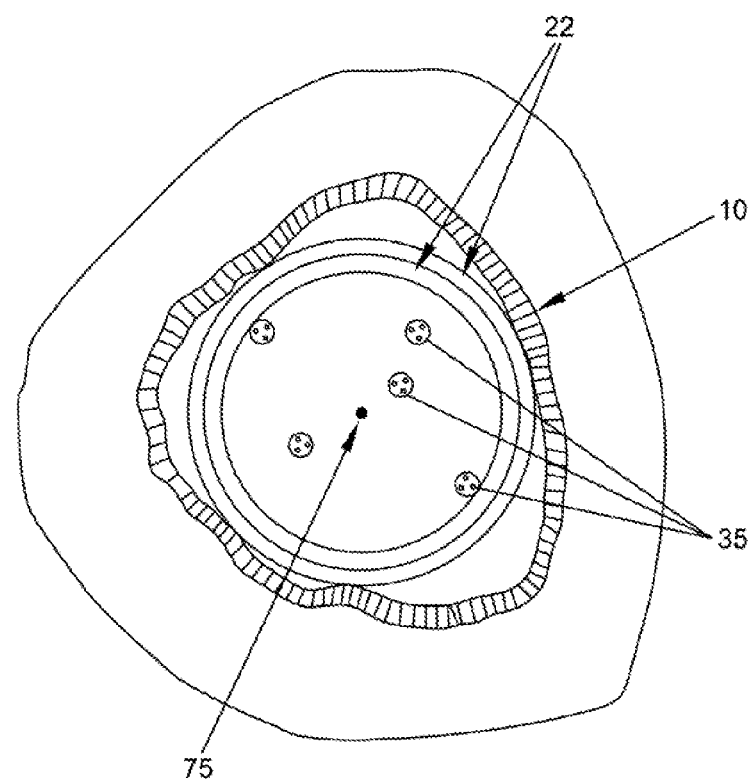
Figure 19:
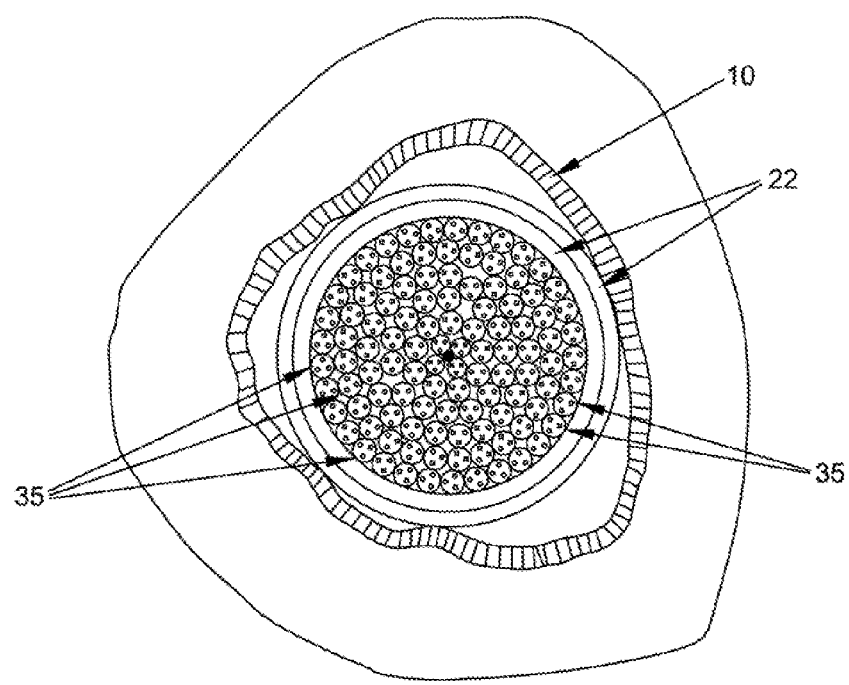

The sixth step is to sequentially introduce the one or more reinforcing elements 15 into the containment bag 10. This is done through the access hole 50 previously created. Note that the flexible nature of the reinforcing elements 15 facilitates their delivery into the containment bag 10 via the access hole 50 previously created. The one or more reinforcing structures 15 are preferably introduced into the containment bag sequentially so as to build up a reinforcing mass. In one preferred form of the invention, and looking now at FIGS. 15 and 16, a plurality of flexible reinforcing sheets 22 (in the form of concentric reinforcing tubes) are sequentially inserted into the containment bag 10, with one flexible reinforcing concentric tube 22 being nested inside another, and a plurality of flexible reinforcing rods 35 are sequentially inserted within the innermost flexible concentric reinforcing tube 22 (FIGS. 17-19). In one preferred form of the invention, the flexible reinforcing sheets 22 (which are preferably in the form of concentric tubes such as is shown in FIGS. 3 and 4 or rolled sheets such as is shown in FIGS. 5 and 6) are delivered to the interior of the containment bag by pushing them out of a delivery tube or, alternatively, by carrying them into the containment bag while held within a delivery tube and then retracting the delivery tube, whereby to expose the flexible reinforcing sheets and allow them to expand. Preferably the size and number of flexible concentric reinforcing tubes 22 and reinforcing rods 35 are selected so as to meet the individual needs of a particular patient. The number of flexible concentric reinforcing tubes 22 utilized in the composite implant, and/or their lengths and/or cross-sectional dimensions, and/or the number of reinforcing rods 35 used, and/or their lengths and/or cross-sectional dimensions, may be selected according to the individual needs of a particular patient. Preferably the number, length, and cross-sectional dimensions of the reinforcing tubes, and the number, length, and cross-sectional dimensions of the reinforcing rods, are selected so as to provide a composite implant having variable stiffness along its length, e.g., a composite implant having a stiffer central region (e.g., 20 GPa) and less stiff distal and proximal ends (e.g., 3 GPa), whereby to prevent stress risers from being created at the ends of the composite implant. To this end, the reinforcing tubes, and the reinforcing rods, are preferably provided in a variety of sizes for appropriate selection by the physician; alternatively, the reinforcing tubes and/or reinforcing rods may be sized at the time of use by the physician. If desired, a guidewire 75 may be provided to facilitate introduction of the one or more reinforcing elements into the containment bag. This guidewire 75 is preferably attached to the distal end of the containment bag 10 using an adhesive or other non-permanent attachment means. After the one or more reinforcement elements 15 have been placed in the containment bag, the guidewire 75 can be detached from the containment bag 10 by pulling or twisting the guidewire. Alternatively, the guidewire 75 may be absorbable, in which case it may be left in the patient at the conclusion of the procedure.

Figure 20:
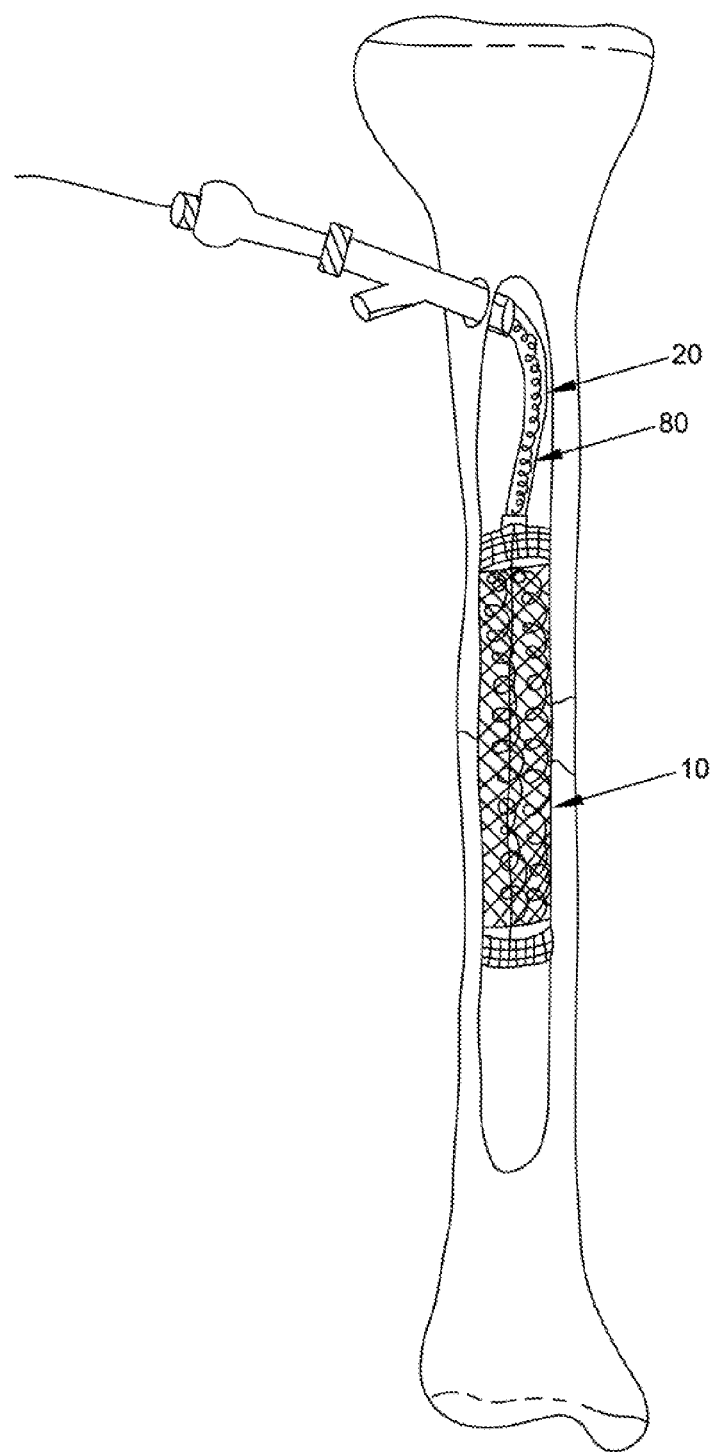
Figure 21:
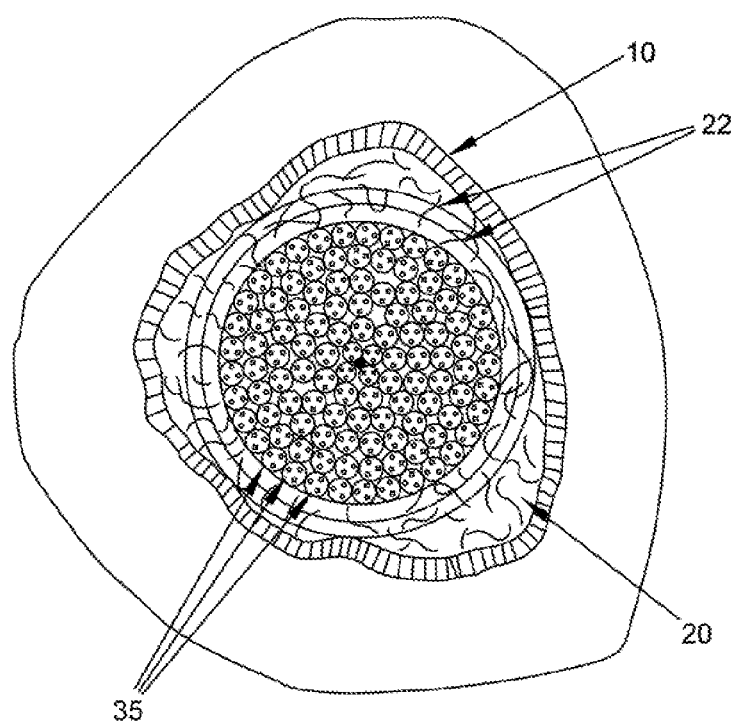

The seventh step is to introduce the injectable matrix material 20 into the containment bag. Again this is done through the access hole 50 previously created. In a preferred form of the invention the injectable matrix material is formed from two or more components that are mixed immediately prior to injection into the patient. This may occur through use of a static mixer fed by multiple syringes. Alternatively the components may be mixed in a bowl and then loaded into a syringe that is connected to the injection tube. In one preferred form of the invention, and looking now at FIGS. 20 and 21, an injection tube 80 is used to deliver the injectable matrix material 20 into the containment bag 10 under pressure, where it flows over and through the one or more reinforcement structures 15 contained within the containment bag 10. The injection tube 80 is withdrawn after the matrix material is injected into the containment bag. The injection tube is, preferably, also capable of transmitting an energy wave into the injectable matrix material in cases where pulsatile flow or the application of vibrational forces is required to aid injecting the matrix material into the containment bag. Suction may be used to facilitate wetting out of the reinforcement structures by removal of trapped air from the composite.

The eighth step is for the injectable matrix material to solidify so that the matrix material 20, the one or more reinforcing elements 15 and the containment bag 10 become a single solidified structure 5 (FIGS. 22 and 23) capable of providing support across the fracture line while the bone fracture heals. If desired, an expandable device (e.g., a balloon) may be used to provide a radial force to aid in the creation of a single integrated structure. More particularly, the expandable device (e.g., balloon) may be used to enhance the penetration of the injectable matrix material into and between one or more reinforcing elements, the containment bag and the bone, and to enhance the interfacial bond between the injectable matrix material and the one or more reinforcing elements, between the injectable matrix material and the containment bag, and between the injectable matrix material and the bone. In the preferred embodiments of the invention this solidification occurs through a chemical reaction that proceeds at a rate that allows sufficient time for injection before the viscosity increases to a point where injection is not possible. Generally this time is five to ten minutes. The solidification occurs within thirty to sixty minutes, although with most chemistries there will be a continuation in strength build-up over a period of hours. In the preferred chemistries the exothermic nature of the reaction is limited to minimize temperature increase in the matrix material to less than 10 degrees C.

Figure 22:
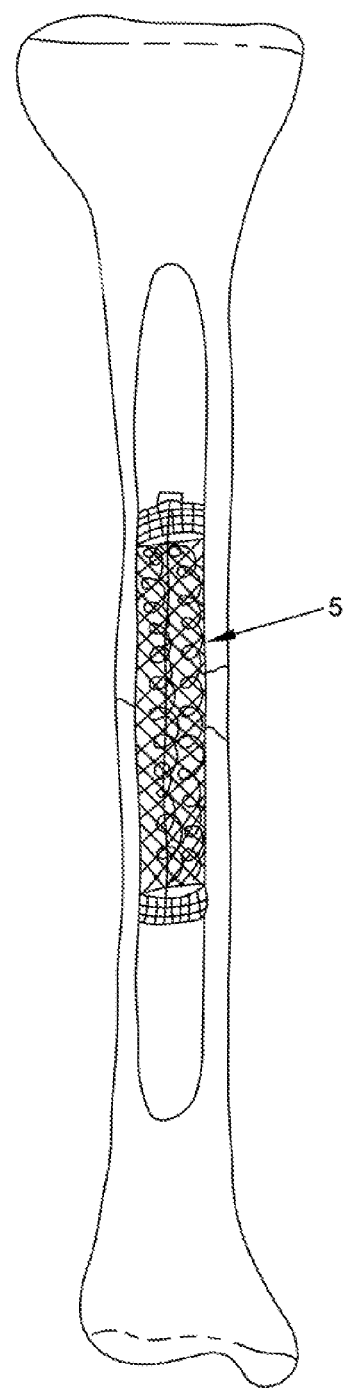
Figure 23:
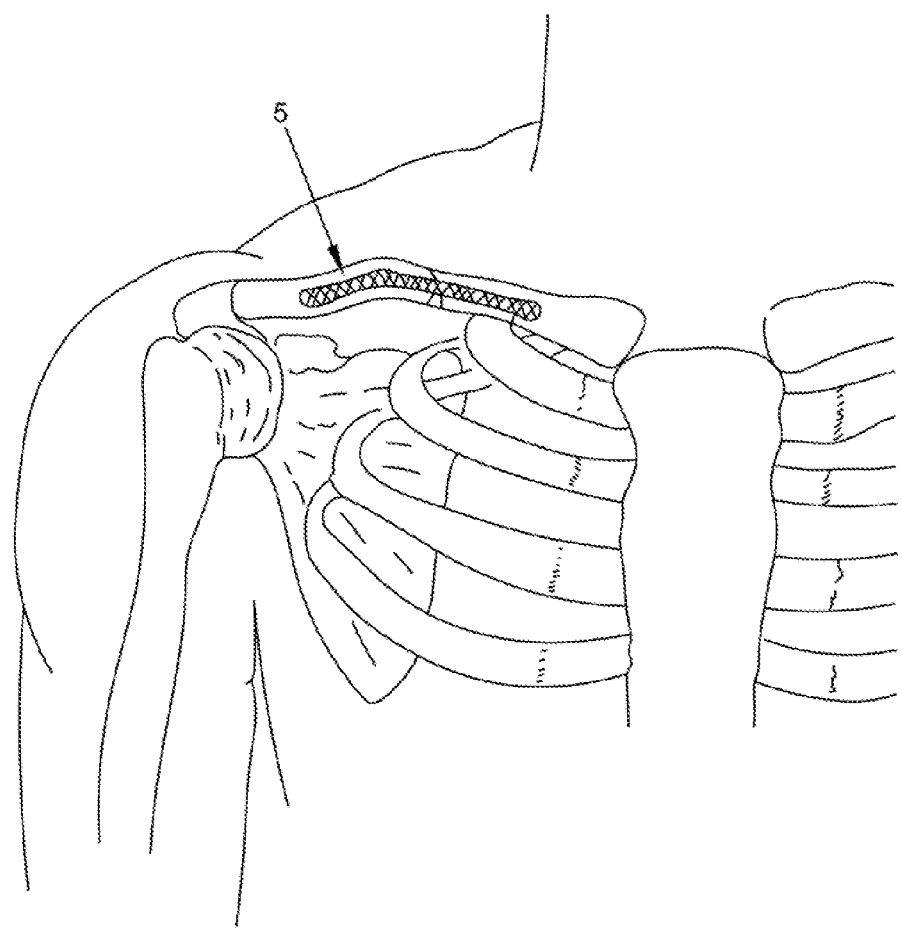

Note how, in FIGS. 22 and 23, the composite implant can contour as needed to the geometry of the intramedullary canal of the bone, i.e., in FIG. 22 the composite implant has a substantially linear shape to match the substantially linear shape of the intramedullary canal of the tibia, whereas in FIG. 23 the composite implant has a contoured shape to match the contour of the clavicle.

The ninth step is to close the wound.

Thus it will be seen that the present invention comprises the provision and use of a novel composite implant for treating bone fractures (and/or for fortifying and augmenting a bone). The composite implant is disposed within the intramedullary canal of the bone (or within another opening in the bone) so as to function as a "splint", whereby to carry the stress created during patient activity. This approach allows the bone fracture to heal (or provides fortification and/or augmentation of a bone) with minimum inconvenience to the patient. The composite implant comprises a plurality of components that are introduced sequentially into the patient, and assembled in situ, thereby allowing the composite implant to be installed using a minimally invasive approach. Significantly, the properties of the composite implant can be custom tailored for different treatment situations, e.g., the composite implant can have different lengths and/or cross-sectional dimensions, the composite implant can have different compressive and/or tensile strengths, etc., all according to the individual needs of a particular patient.

Additional Constructions

It should be appreciated that, if desired, containment bag 10 may be omitted. In this case, the one or more reinforcing elements 15 and injectable matrix material 20 are deployed directly into the intramedullary canal (or other opening) in the bone that is being treated, without an intervening containment bag 10.

Figure 24:
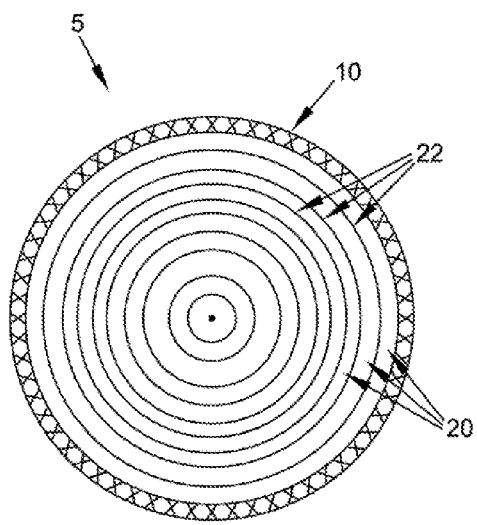
FIGS. 24-26 show alternative forms of the composite implant of the present invention.
Figure 25:
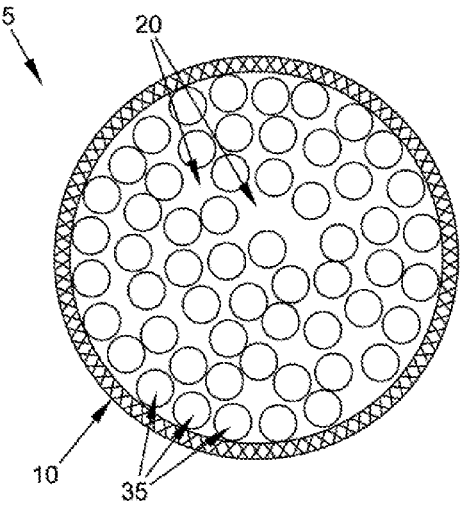
Figure 26:
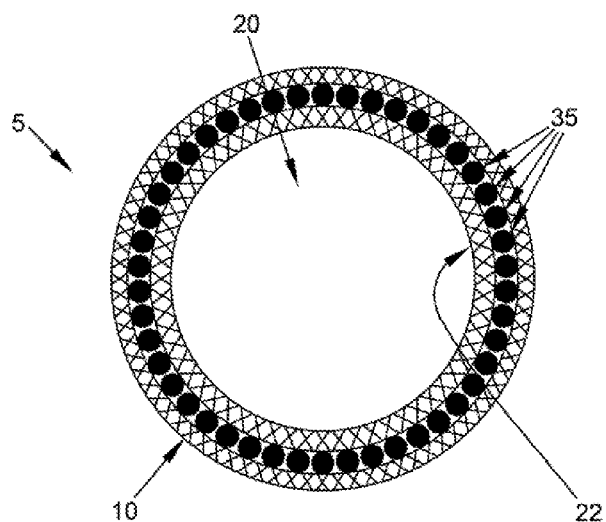

Furthermore, it should be appreciated that, if desired, composite implant 5 may be formed out of flexible reinforcing sheets 22 without any flexible reinforcing rods 35 (FIG. 24); with flexible reinforcing rods 35 and without any flexible reinforcing sheets 22 (FIG. 25); and with a laminated construction comprising both flexible reinforcing sheets 22 and flexible reinforcing rods 35 (FIG. 26).

Figure 27:
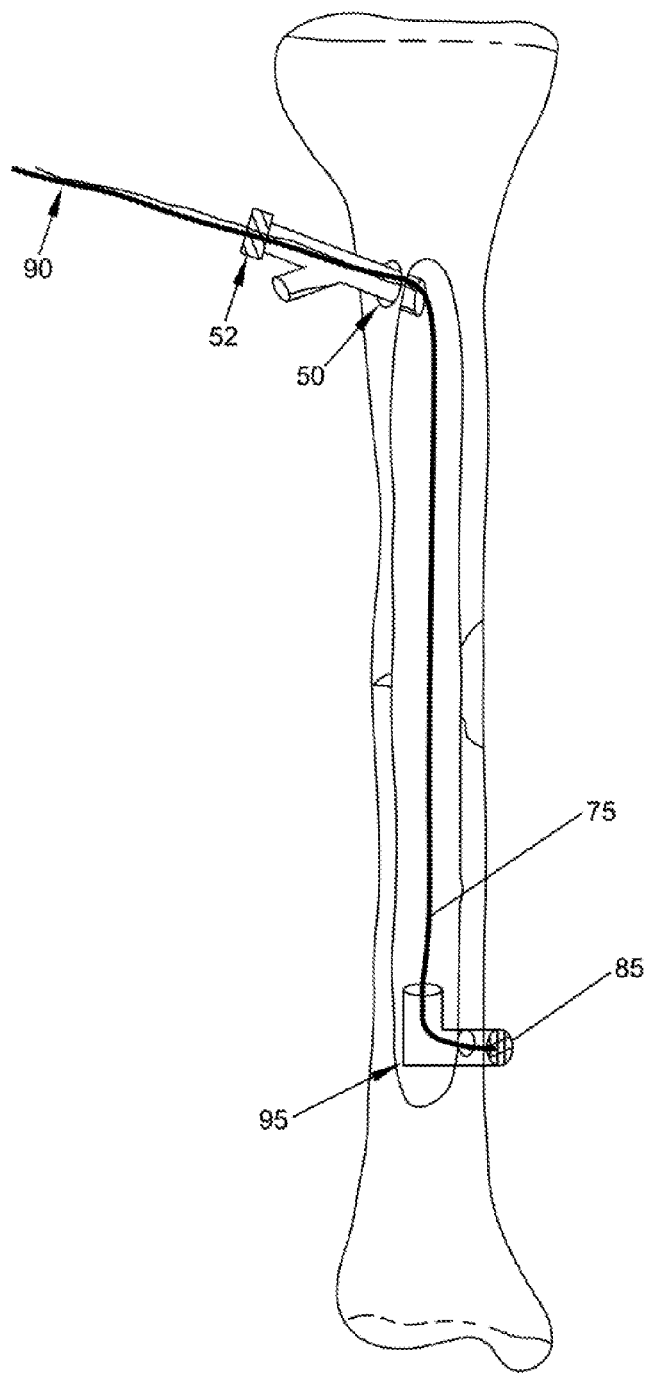
FIG. 27 shows how the guidewire used to deliver the composite implant may also be used to reduce a fracture and/or to help stabilize the fracture.

In addition, FIG. 27 shows how guidewire 75 may be used to reduce a fracture prior to delivery of the composite implant. More particularly, in this form of the invention, guidewire 75 has an enlargement 85 formed at one end, with enlargement 85 being disposed exterior to the bone being treated, and with the opposite end 90 of guidewire 75 emerging from port 52. As a result of this configuration, by applying tension to end 90 of guidewire 75, the fracture can be reduced and the tensioned guidewire 75 can help support the bone. In one preferred form of the invention, a fixture 95 may be positioned within the intramedullary canal of the bone, adjacent to enlargement 85, so as to direct guidewire 75 along the longitudinal channel of the bone and thereby facilitate fracture reduction and delivery of the composite.

EXAMPLES

Example 1

Preparation of 50/50 prepolymer: 10.60 g polycaprolactone diol (0.02 mol), 6.00 g polycaprolactone triol (0.02 mol), both previously vacuum dried and 23.31 mL isophorone diisocyanate (0.10 mol) were stirred continuously while heating slowly to 70° C., and then stirred at 70° C. for 2 hours. The heat and stirring was stopped and the reaction was allowed to sit at room temperature overnight. Yield ~40 g clear highly viscous material.

Example 2

Preparation of 60/40 prepolymer: 15.90 g polycaprolactone diol (0.03 mol), 6.00 g polycaprolactone triol (0.02 mol), both previously vacuum dried and 27.97 mL isophorone diisocyanate (0.13 mol) were stirred continuously while heating slowly to 70° C., and then stirred at 70° C. for 2 hours. The heat and stirring was stopped and the reaction was allowed to sit at room temperature overnight. Yield ~50 g clear viscous material.

Example 3

Preparation of hexamethylenediamine aspartic acid ester: 11.62 g hexamethylenediamine (0.10 mol) and 38.86 g tert-butanol was combined, and 34.46 g diethyl maleate (0.20 mol) was added slowly. Reaction was $N_2$ blanketed and heated to 70° C. with stifling for 30 minutes. Reaction was allowed to sit at room temperature for 120 hours before removing tert-butanol via rotary evaporation at 70° C. and 215-195 mbar. Yield ~45 mL clear slightly viscous liquid.

Example 4

Preparation of isophorone diamine aspartic acid ester: 17.04 g isophorone diamine (0.10 mol) and 38.75 g tert-butanol was combined, and 34.43 g diethyl maleate (0.20 mol) was added slowly. Reaction was $N_2$ blanketed and heated to 35° C. with stifling for 15 minutes. Reaction was allowed to sit at room temperature for 120 hours before removing tert-butanol via rotary evaporation at 70° C. and 215-195 mbar. Yield ~45 mL clear slightly viscous liquid.

Example 5

Preparation of diethylenetriamine aspartic acid ester: 10.33 g diethylenetriamine (0.10 mol) and 38.74 g tert-butanol was combined, and 34.36 g diethyl maleate (0.20 mol) was added slowly. Reaction was $N_2$ blanketed and heated to 35° C. with stifling for 10 minutes. Reaction was allowed to sit at room temperature for 120 hours before removing tert-butanol via rotary evaporation at 70° C. and 215-195 mbar. Yield ~35 mL pale yellow slightly viscous liquid.

Example 6

Preparation of Polypropylene braid: A Steeger horizontal braider was used with 0.008" OD polypropylene monofilament. Braids were run with 24 sheath yarns, and the samples that were run with axials had 12 axials, all made of the same 0.008" OD PP. Samples were run over 5 mm and 10 mm diameter mandrels.

Example 7

Preparation of Polylactic acid (PLA) braid: A Steeger horizontal braider was used with 120d PLLA multifilament. Braids were run with 48 ends, and the samples that were run with axials had 24 axials, all made of the same 120d PLLA. Samples were run over 5, 7 and 10 mm diameter mandrels.

Example 8

Preparation of 1.5 mm diameter PLA braid: 1.5 mm braids were constructed around a core constructed of 90 ends of 75d PLLA, twisted at approximately 2 TPI. The outer sheath was constructed of 24 ends of 120d PLLA. A Steeger 48 end horizontal braider was used.

Example 9

Preparation of 1.5 mm diameter PLA braid with axial fibers: 1.5 mm braids were constructed around a core constructed of 90 ends of 75d PLLA, twisted at approximately 2 TPI. The outer sheath was constructed of 24 ends of 120d PLLA, and 12 axial ends of 120d PLLA. A Steeger 48 end horizontal braider was used.

Example 10

Preparation of Polyurethane: 2.60 grams of the prepolymer of Example 1 was mixed with 0.30 grams of polycaprolactone triol and 0.10 grams of glycerol at 0.13% w/w dibutyltin dilaurate. The mixture was transferred into a 3 ml syringe and placed in an oven at 37° C. to cure overnight. The sample was removed from the syringe and cut using a diamond saw to make a compression test piece. Compression testing showed that the material had a compressive stiffness of 1.1 GPa and a yield strength of 56 MPa.

Example 11

Preparation of Polyurethane: 2.60 grams of the prepolymer of Example 1 was mixed with 1.00 grams of tricalcium phosphate and 0.30 grams of polycaprolactone triol and 0.10 grams of glycerol at 0.13% w/w dibutyltin dilaurate. The mixture was transferred into a 3 ml syringe and placed in an oven at 37° C. to cure overnight. The sample was removed from the syringe and cut using a diamond saw to make a compression test piece. Compression testing showed that the material had a compressive stiffness of 1.3 GPa and a yield strength of 63 MPa.

Example 12

Preparation of Polyurethane: 2.60 grams of the prepolymer of Example 1 was mixed with 2.48 grams of tricalcium phosphate and 0.35 grams of polycaprolactone triol and 0.10 grams of glycerol 0.13% w/w dibutyltin dilaurate. The mixture was transferred into a 3 ml syringe and placed in an oven at 37° C. to cure overnight. The sample was removed from the syringe and cut using a diamond saw to make a compression test piece. Compression testing showed that the material had a compressive stiffness of 1.8 GPa and a yield strength of 71 MPa.

Example 13

Preparation of Polyurethane: 4.05 grams of the prepolymer of Example 2 was mixed with 0.50 grams of polycaprolactone triol and 0.15 grams of glycerol 0.13% w/w dibutyltin dilaurate. The mixture was transferred into a 3 ml syringe and placed in an oven at 37° C. to cure overnight. The sample was removed from the syringe and cut using a diamond saw to make a compression test piece. Compression testing showed that the material had a compressive stiffness of 1.1 GPa and a yield strength of 53 MPa.

Example 14

Preparation of Polyurethane: 4.05 grams of the prepolymer of Example 2 was mixed with 2.01 grams of tricalcium phosphate and 0.50 grams of polycaprolactone triol and 0.15 grams of glycerol 0.13% w/w dibutyltin dilaurate. The mixture was transferred into a 3 ml syringe and placed in an oven at 37° C. to cure overnight. The sample was removed from the syringe and cut using a diamond saw to make a compression test piece. Compression testing showed that the material had a compressive stiffness of 1.5 GPa and a yield strength of 69 MPa.

Example 17

Preparation of Polyurethane: 5.26 grams of the prepolymer of Example 1 was mixed with 3.81 grams of the aspartic acid ester from Example 5. The mixture was transferred to a 3 ml syringe and placed in an oven at 37° C. to cure overnight. The sample was removed from the syringe and cut using a diamond saw to make a compression test piece. Compression testing showed that the material had a compressive stiffness of 0.6 GPa and a yield strength of 29 MPa.

Example 18

Preparation of Polyurethane: 2.05 grams of the prepolymer of Example 2 was mixed with 2.17 grams of the aspartic acid ester from Example 3. The mixture was transferred to a 3 ml syringe and placed in an oven at 37° C. to cure overnight.

Example 19

Preparation of Polyurethane: 2.03 grams of the prepolymer of Example 2 was mixed with 2.43 grams of the aspartic acid ester from Example 4. The mixture was transferred to a 3 ml syringe and placed in an oven at 37° C. to cure overnight.

Example 20

Preparation of Polyurethane: 8.10 grams of the prepolymer of Example 2 was mixed with 5.70 grams of the aspartic acid ester from Example 5. The mixture was transferred to a 3 ml syringe and placed in an oven at 37° C. to cure overnight. The sample was removed from the syringe and cut using a diamond saw to make a compression test piece. Compression testing showed that the material had a compressive stiffness of 0.7 GPa and a yield strength of 20 MPa.

Example 21

Preparation of high MW DL-lactide: 5.15 grams of DL-lactide monomer was added to 0.31 grams ethylene glycol and 0.0016 grams Tin(II) 2-ethylhexanoate. Mixture heated to 120° C. for 24 hours. Clear, viscous fluid.

Example 22

Preparation of middle MW DL-lactide: 7.19 grams of DL-lactide monomer was added to 1.56 grams ethylene glycol and 0.0029 grams Tin(II) 2-ethylhexanoate. Mixture heated to 120° C. for 24 hours. Clear, slightly viscous fluid.

Example 23

Preparation of low MW DL-lactide: 7.21 grams of DL-lactide monomer was added to 3.10 grams ethylene glycol and 0.0030 grams Tin(II) 2-ethylhexanoate. Mixture heated to 120° C. for 24 hours. Clear fluid, very low viscosity.

Example 24

Preparation of Polyurethane: 2.05 grams of prepolymer from Example 2 was mixed with 0.59 grams DL-lactide from Example 21 and 0.0031 grams dibutyltin dilaurate. The mixture was transferred to a 3 ml syringe and placed in an oven at 37° C. to cure overnight.

Example 25

Preparation of Polyurethane: 2.02 grams of prepolymer from Example 2 was mixed with 0.57 grams DL-lactide from Example 22 and 0.0032 grams dibutyltin dilaurate. The mixture was transferred to a 3 ml syringe and placed in an oven at 37° C. to cure overnight.

Example 26

Preparation of Polyurethane: 2.05 grams of prepolymer from Example 2 was mixed with 0.57 grams DL-lactide from Example 23 and 0.0024 grams dibutyltin dilaurate. The mixture was transferred to a 3 ml syringe and placed in an oven at 37° C. to cure overnight.

Example 27

Preparation of Polyurethane with braid reinforcement: One 10 mm ID polypropylene braid with triaxials was filled with polyurethane from Example 13. Sample was cured at 37° C. in a cylindrical mold overnight. The sample was removed from the syringe and cut using a diamond saw to make a compression test piece. Compression testing showed that the material had a compressive stiffness of 1.3 GPa and a yield strength of 69 MPa.

Example 28

Preparation of Polyurethane with braid reinforcement: Two 10 mm ID polypropylene braids with triaxials were stacked one inside the other and filled with polyurethane from Example 13. Sample was cured at 37° C. in a cylindrical mold overnight. The sample was removed from the syringe and cut using a diamond saw to make a compression test piece. Compression testing showed that the material had a compressive stiffness of 1.0 GPa and a yield strength of 44 MPa.

Example 29

Preparation of Polyurethane with braid reinforcement: Four 10 mm ID polypropylene braids with triaxials were stacked one inside the other and filled with polyurethane from Example 13. Sample was cured at 37° C. in a cylindrical mold overnight. The sample was removed from the syringe and cut using a diamond saw to make a compression test piece. Compression testing showed that the material had a compressive stiffness of 1.3 GPa and a yield strength of 69 MPa.

Example 30

Preparation of Polyurethane with braid reinforcement: Four 10 mm ID polypropylene braids with triaxials were stacked one inside the other, and three 5 mm ID polypropylene braids with triaxials were stacked in the same way. The smaller ID braids were placed inside the four 10 mm ID braids and filled with polyurethane from Example 13. Sample was cured at 37° C. in a cylindrical mold overnight. The sample was removed from the syringe and cut using a diamond saw to make a compression test piece. Compression testing showed that the material had a compressive stiffness of 1.2 GPa and a yield strength of 63 MPa.

Example 31

Preparation of Polyurethane with braid reinforcement: One 10 mm ID polypropylene braid with triaxials was filled with polyurethane from Example 14. Sample was cured at 37° C. in a cylindrical mold overnight. The sample was removed from the syringe and cut using a diamond saw to make a compression test piece. Compression testing showed that the material had a compressive stiffness of 1.0 GPa and a yield strength of 53 MPa.

Example 32

Preparation of Polyurethane with braid reinforcement: Two 10 mm ID polypropylene braids with triaxials were stacked one inside the other and filled with polyurethane from Example 14. Sample was cured at 37° C. in a cylindrical mold overnight. The sample was removed from the syringe and cut using a diamond saw to make a compression test piece. Compression testing showed that the material had a compressive stiffness of 1.7 GPa and a yield strength of 75 MPa.

Example 33

Preparation of Polyurethane with braid reinforcement: Four 10 mm ID polypropylene braids with triaxials were stacked one inside the other and filled with polyurethane from Example 14. Sample was cured at 37° C. in a cylindrical mold overnight. The sample was removed from the syringe and cut using a diamond saw to make a compression test piece. Compression testing showed that the material had a compressive stiffness of 2.0 GPa and a yield strength of 66 MPa.

Example 34

Preparation of Polyurethane with braid reinforcement: Four 10 mm ID polypropylene braids with triaxials were stacked one inside the other, and three 5 mm ID polypropylene braids with triaxials were stacked in the same way. The smaller ID braids were placed inside the four 10 mm ID braids and filled with polyurethane from Example 14. Sample was cured at 37° C. in a cylindrical mold overnight. The sample was removed from the syringe and cut using a diamond saw to make a compression test piece. Compression testing showed that the material had a compressive stiffness of 1.7 GPa and a yield strength of 70 MPa.

Example 35

Preparation of Polyurethane with braid reinforcement: One 1.5 mm ID PLA braid with axials was loaded into a 2 mm ID tube and filled with polyurethane from Example 13 that had been degassed with no DBDL. Sample was cured at 70° C. for two days. The sample was removed from the tubing for three point bending test.

Example 36

Preparation of Polyurethane with braid reinforcement: One 1.5 mm ID PLA braid without axials was loaded into a 2 mm ID tube and filled with polyurethane from Example 13 that had been degassed with no DBDL. Sample was cured at 70° C. for two days. The sample was removed from the tubing for three point bending test.

Example 37

Preparation of Polyurethane with braid reinforcement: One 5 mm ID PLA braid without axials was loaded into a 5 mm ID tube and filled with polyurethane from Example 13 that had been degassed with no DBDL. Sample was cured at 70° C. for two days. The sample was removed from the tubing for three point bending test. Three point bend testing showed that the material had a stiffness of 1.2 Gpa and a yield strength of 39 Mpa.

Example 38

Preparation of Polyurethane with braid reinforcement: One 10 mm ID PLA braid without axials was filled with polyurethane from Example 13 that had been degassed with no DBDL. Sample was cured at 70° C. in a cylindrical mold for two days. The sample was removed from the syringe and cut using a diamond saw to make a compression test piece. Compression testing showed that the material had a compressive stiffness of 0.8 GPa and a yield strength of 39 MPa.

Example 39

Preparation of Polyurethane with braid reinforcement: One 7 mm ID PLA braid without axials was placed inside of a 10 mm ID PLA braid without axials and filled with polyurethane from Example 13 that had been degassed with no DBDL. Sample was cured at 70° C. in a cylindrical mold for two days.

The sample was removed from the syringe and cut using a diamond saw to make a compression test piece. Compression testing showed that the material had a compressive stiffness of 0.5 GPa and a yield strength of 27 MPa.

Example 40

Preparation of Polyurethane with braid reinforcement: One 5 mm ID PLA braid without axials was placed inside of a 7 mm ID PLA braid without axials and both braids were placed inside of a 10 mm ID PLA braid without axials, and the entire stack was filled with polyurethane from Example 13 that had been degassed with no DBDL. Sample was cured at 70° C. in a cylindrical mold for two days. The sample was removed from the syringe and cut using a diamond saw to make a compression test piece. Compression testing showed that the material had a compressive stiffness of 0.8 GPa and a yield strength of 39 MPa.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for treating a bone fracture, and/or fortifying bone and/or augmenting bone, the method comprising:
  selecting at least one reinforcing element to be combined with an injectable matrix material and with a containment bag so as to together form a biodegradable composite implant capable of supporting the bone, wherein the composite implant has a stiffer central region and less stiff distal and proximal ends, wherein the at least one reinforcing element is flexible;
  positioning the entire containment bag in a cavity in the bone, and positioning the at least one reinforcing element in the containment bag; and
  flowing the injectable matrix material into the containment bag so that the injectable matrix material interfaces with the at least one reinforcing element and with the containment bag so as to form the biodegradable composite implant;
  wherein the injectable matrix material is configured to thereafter transform from a flowable state to a non-flowable state so as to establish a static structure for the biodegradable composite implant, such that the biodegradable composite implant supports the adjacent bone;
  wherein the containment bag comprises a resorbable polymer selected from the group consisting of polyurethane, polylactic acid, polyglycolic acid and mixtures or copolymers thereof; and
  wherein the containment bag controls the degradation of the composite implant by modulating the ingress of fluid into the containment bag.

2. A method according to claim 1 wherein the cavity in the bone comprises the intramedullary canal.

3. A method according to claim 2 wherein the intramedullary canal is accessed through a hole having a diameter smaller than the diameter of the intramedullary canal.

4. A method according to claim 3 wherein the hole extends at an acute angle to the intramedullary canal.

5. A method according to claim 3 wherein the at least one reinforcing element must be flexed in order to pass through the hole and into the intramedullary canal.

6. A method according to claim 3 wherein the at least one reinforcing element comprises a plurality of reinforcing elements, wherein each of the reinforcing elements is individually capable of being passed through the hole, and further wherein the plurality of reinforcing elements collectively form a structure too large to be passed through the hole.

7. A method according to claim 1 wherein the at least one reinforcing element is flexible both radially and longitudinally.

8. A method according to claim 1 wherein the at least one reinforcing element comprises at least one from the group consisting of a flexible reinforcing sheet, a flexible reinforcing rod, and particulates.

9. A method according to claim 8 wherein the at least one reinforcing element comprises a flexible reinforcing sheet in the form of a tube.

10. A method according to claim 9 wherein the at least one reinforcing element comprises at least two flexible reinforcing sheets arranged concentrically.

11. A method according to claim 8 wherein the at least one reinforcing element comprises a flexible reinforcing sheet in the form of a rolled sheet.

12. A method according to claim 8 wherein the at least one reinforcing element comprises a flexible reinforcing sheet having an arcuate cross-section.

13. A method according to claim 8 wherein the at least one reinforcing element comprises a flexible reinforcing sheet having a planar cross-section.

14. A method according to claim 8 wherein the at least one reinforcing element comprises a flexible reinforcing sheet comprising filaments formed into a textile.

15. A method according to claim 8 wherein the at least one reinforcing element comprises a flexible reinforcing sheet comprising filaments connected by a film.

16. A method according to claim 8 wherein the at least one reinforcing element comprises particulates.

17. A method according to claim 8 wherein the at least one reinforcing element comprises a flexible reinforcing rod comprising filaments held together.

18. A method according to claim 17 wherein the at least one reinforcing element comprises a flexible reinforcing rod and the filaments are held together by an outer sheath.

19. A method according to claim 18 wherein the outer sheath comprises filaments formed into a textile.

20. A method according to claim 17 wherein the at least one reinforcing element comprises a flexible reinforcing rod and the filaments are held together by a compacted connecting structure of a textile or film.

21. A method according to claim 20 wherein the connecting structure is compacted by at least one of winding and compressing.

22. A method according to claim 17 wherein the at least one reinforcing element comprises a flexible reinforcing rod and the filaments are held together by a binder.

23. A method according to claim 1 wherein the at least one reinforcing element comprises at least one flexible reinforcing sheet and at least one flexible reinforcing rod.

24. A method according to claim 23 wherein the at least one flexible reinforcing sheet and the at least one flexible reinforcing rod are selected so as to form the composite implant with a desired stiffness.

25. A method according to claim 1 wherein the injectable matrix material comprises a polymer.

26. A method according to claim 1 wherein the at least one reinforcing element is positioned in the containment bag after the containment bag has been positioned in the cavity in the bone.

27. A method according to claim 1 wherein the at least one reinforcing element is bioabsorbable.

28. A method according to claim 1 wherein the injectable polymer matrix is biodegradable with an average molecular weight of 50 to 50000.

* * * * *